US007283244B2

(12) United States Patent
Takagi

(10) Patent No.: US 7,283,244 B2
(45) Date of Patent: Oct. 16, 2007

(54) REFLECTANCE ESTIMATING METHOD

(75) Inventor: Atsushi Takagi, Aichi-ken (JP)

(73) Assignee: Toyota Jidosha Kabushiki Kaisha (JP)

( * ) Notice: Subject to any disclaimer, the term of this patent is extended or adjusted under 35 U.S.C. 154(b) by 318 days.

(21) Appl. No.: 10/411,276

(22) Filed: Apr. 11, 2003

(65) Prior Publication Data
US 2003/0193669 A1     Oct. 16, 2003

(30) Foreign Application Priority Data
Apr. 12, 2002 (JP) .............................. 2002-111140

(51) Int. Cl.
*G01N 21/55*     (2006.01)
*G01N 21/47*     (2006.01)

(52) U.S. Cl. ..................................... 356/446; 356/445

(58) Field of Classification Search ................ 356/319, 356/402, 405, 406, 408, 421, 422, 423, 425, 356/445–448; 250/226
See application file for complete search history.

(56) References Cited

U.S. PATENT DOCUMENTS

| 4,479,718 | A | | 10/1984 | Alman |
| 4,711,580 | A | | 12/1987 | Venable |
| 4,992,963 | A | * | 2/1991 | Funt et al. .................. 382/162 |
| 5,412,465 | A | * | 5/1995 | Baylor et al. ............... 356/301 |
| 6,166,814 | A | | 12/2000 | Pringle |
| 6,249,751 | B1 | * | 6/2001 | Asaba et al. ................. 702/76 |
| 6,362,885 | B1 | | 3/2002 | Osumi et al. |
| 6,750,970 | B2 | * | 6/2004 | Masuda ....................... 356/402 |
| 6,788,413 | B2 | * | 9/2004 | Torfs et al. .................. 356/408 |
| 2004/0090640 | A1 | * | 5/2004 | Nino et al. ................... 358/1.9 |

FOREIGN PATENT DOCUMENTS

| JP | A 03-135740 | | 6/1991 |
| JP | 10010045 A | * | 1/1998 |
| JP | 11-230831 | | 8/1999 |
| JP | 11211569 A | * | 8/1999 |

(Continued)

OTHER PUBLICATIONS

Saito et al., "Recovery of Shape and Surface Reflectance of Specular Object from Rotation of Light Source," May 1999, XP-001001275, Department of Information and Computer Science, Keio University, Japan.*

(Continued)

*Primary Examiner*—Gregory J. Toatley, Jr.
*Assistant Examiner*—Gordon J. Stock, Jr.
(74) *Attorney, Agent, or Firm*—Finnegan, Henderson, Farabow, Garrett & Dunner, LLP

(57) ABSTRACT

At first, a sample for obtaining light measurement data is set to obtain reflectances. After setting an arbitrary wavelength $\lambda_i$, a principal component analysis is executed to obtain an eigenvalue 1 and an eigenvector b. Then a basic equation for reflectance is determined by deriving a coefficient k, utilizing a known reflectance of an object of which reflectance is to be estimated. Thereafter a process of deriving a reflectance at an arbitrary displacement angle is executed for all the wavelengths, for example over a visible wavelength range. In this manner, the reflectance of an object at an arbitrary displacement angle can easily be obtained by utilizing the basic equation for the reflectance derived from the eigenvector obtained from the principal component analysis of the measured data.

17 Claims, 15 Drawing Sheets

FOREIGN PATENT DOCUMENTS

| JP | 11-311573 | 11/1999 |
| JP | 11351964 A * | 12/1999 |
| WO | WO 02/14812 | 2/2002 |

OTHER PUBLICATIONS

European Search Report for EP 03 00 8355 dated Mar. 10, 2004.*

Imai, F. H., et al., "A Comparative Analysis of Spectral Reflectance Estimated in Various spaces Using a Trichromatic Camera System," *J. Imaging Sci. & Tech.*, vol. 44, No. 4 (Jul./Aug. 2000), pp. 280-287.

Miyake, Y., et al., "Gonio-Photometric Imaging for Recording of Reflectance Spectra of Three Dimensional Object," *Spectral Vision*, No. 1, 2001, XP002273039, p. 4.

Vrhel, M. J., et al., "Color Correction Using Principal Components," *Color Research and application*, J. Wiley & Sons, Inc., New York, vol. 17, No. 5 (Oct. 1, 1992), pp. 328-338.

Fairchild, M.D., et al., "Absolute Reflectance Factor Calibration for Goniospectrophotometry," *Color Res. & Appln.*, vol. 15, No. 6, 1990, pp. 311-320.

Japanese Office Action dated May 30, 2006, of JP2002-111140.

* cited by examiner

10···KEYBOARD

12···COMPUTER MAIN BODY

14···CRT

16···PERSONAL COMPUTER

X···VECTOR a···DISTANCE b···UNIT VECTOR (EIGENVECTOR)

24···DIRECTION OF REGULAR REFLECTION

λ···EIGENVALUE 30, 32, 34···CHARACTERISTIC CURVE

REFLECTANCE ESTIMATING METHOD

BACKGROUND OF THE INVENTION

1. Field of the Invention

The present invention relates to a reflectance estimating method, and more particularly to a reflectance estimating method for estimating a reflectance of an object at an arbitrary displacement angle which displacement angle is an angle representing displacement from the direction of a regular reflection of light from the object.

2. Description of the Related Art

In the field of computer graphics (so-called CG) which enable presentation of an image display with colors on a computer or printing of such image, there are executed an image display of patterns or graphics of various colors and a printing of the displayed color image. In the case of displaying an object as a colored image, the object is presented by luminance of the light through modeling the principle of light reflection, but the color of the object cannot be sufficiently represented by the luminance presentation only of the object, and in such a case, it is difficult to obtain a substantial color presentation (color reproduction) of the object.

In order to obtain a color reproduction exactly representing the appearance of the object under an arbitrary environment, it is necessary to consider not only the reflectance in a normal reflecting direction what is ordinarily employed as the reflectance, but also a reflectance at a displacement angle, which is an angle representing displacement from the normal light reflecting direction of the object (for example spectral steric angle reflectance).

However, a determination of the reflectance for each displacement angle requires an enormous amount of data and is scarcely practical.

For this reason, there is proposed a reflectance measuring method, in which the reflectances are measured corresponding to randomly selected plural displacement angles and the measured data are used to estimate a reflectance corresponding to another displacement angle (cf. JP-A No. 11-230831). This measuring method estimates the reflectance of a displacement angle other than the selected ones, by an interpolation process utilizing colorimetry values obtained in directions of a predetermined number.

However, since the reflectance of an object is not linear nor regular, a large number of samples (displacement angles) have to be selected in order to achieve a highly precise estimation in the prior measuring method. Therefore, in order to estimate an arbitrary color (reflectance) with a certain precision, it is necessary to in advance prepare data measured in a large number of displacement angles and to use such data in the determination of the reflectance, so that the determination of the reflectance has not been possible in an efficient manner.

Also in considering the reflectance at a displacement angle, a light incident angle to the object is often selected at 45°, but a light receiving angle (displacement angle) for measuring the reflectance is not generally defined. It is different depending on the measuring apparatus used or on the measuring method. In this manner, there has not been considered the properness of the light receiving angle (displacement angle) for measuring the reflectance, which is to be used for estimating the reflectance at an arbitrary displacement angle.

For example, there is already known a technology (U.S. Pat. No. 4,479,718) for estimating the reflectance on a solid surface or a metallic coated surface, and this technology utilizes 15°, 45° and 110° as displacement angles. In this technology, however, since the displacement angles determined for a solid or metallic coated surface are empirically handled, an obtained result cannot be ensured for a change in the displacement angle. It is also difficult to estimate a reflectance on an arbitrary object surface.

SUMMARY OF THE INVENTION

In consideration of the foregoing, an object of the present invention is to provide a method for estimating the reflectance which is usable for faithful presentation of a color of an object.

For attaining the object mentioned above, the present invention is featured by following (1) to (14):

(1) A reflectance estimating method for estimating a reflectance at an arbitrary displacement angle $\alpha$ which is an angle representing displacement from a normal light reflecting direction of an object, the method including (a) a step of executing a principal component analysis on reflectances at predetermined plural displacement angles, (b) a step of selecting a principal component vector obtained by the analysis as an eigenvector b, and (c) a step of estimating a reflectance at a displacement angle other than the predetermined displacement angles, at least based on the eigenvector.

The reflectance estimating method according to (1) estimates the reflectance at an arbitrary displacement angle. At first a principal component analysis is executed on the reflectances at predetermined plural displacement angles. The principal component analysis is an analysis for extracting a feature of the data, and, in the present invention, provides a feature of the reflectance as a collection of the reflectances for the plural displacement angles. Stated otherwise, a principal component vector obtained as a result of the analysis represents the feature of the reflectance corresponding to the displacement angle.

Thus, the principal component vector obtained as the result of the principal component analysis is taken as a eigenvector, and the reflectance at a displacement angle other than the aforementioned predetermined displacement angles is estimated at least based on such eigenvector.

Since the eigenvector contains the feature of the reflectance for the displacement angle, it functions effectively also for a displacement angle other than those used for determining the eigenvector. Therefore, such eigenvector allows to estimate the reflectance at a displacement angle other than the predetermined displacement angles mentioned before. For the reflectance, there may be used a spectral steric angle reflectance.

(2) In the reflectance estimating method described in (1), the principal component analysis step (a) includes a step of entering predetermined reflectances of an object, executing a principal component analysis on such reflectances thereby obtaining a principal component as an eigenvalue and a principal component vector as an eigenvector, and estimating the reflectance at a displacement angle other than the aforementioned predetermined displacement angles based on such eigenvalue and such eigenvector.

The entry of a known reflectance of a predetermined object, in a number sufficient for analysis, allows the execution of the aforementioned principal component analysis. A principal component and a principal component vector obtained by the principal component analysis on these reflectances are determined as an eigenvalue and an eigenvector. Thus, based on these eigenvalue and eigenvector, the reflectance can be estimated at a displacement angle other than the predetermined displacement angles.

(3) The reflectance estimating step described in (2) includes a step of determining a basic equation on the reflectance represented by the eigenvalue, the eigenvector and a coefficient to be multiplied on the eigenvector and estimating, from such basic equation, the reflectance at a displacement angle other than the predetermined displacement angles.

As regards the reflectance, at least a feature amount represented by the eigenvector can be extracted by the principal component analysis. Therefore, the reflectance can be replaced by a vector presentation utilizing the eigenvector. In such vector presentation, in order to correlate the eigenvalue and the eigenvector with the reflectance, it is necessary to determine a coefficient for to be multiplied on the eigenvector.

Therefore, there is determined a basic equation on the reflectance, represented by the eigenvalue, the eigenvector and a coefficient to be multiplied on the eigenvector. Such basic equation allows to derive the reflectance from the result of detection of the principal component analysis. Thus the reflectance can be estimated from the basic equation, at a displacement angle other than the predetermined displacement angles.

(4) The reflectance estimating method described in (2) or (3) includes a step of determining a basic equation on the reflectance, which basic equation includes an average value vector obtained by the principal component analysis on the reflectance, and estimating, from such basic equation, the reflectance at a displacement angle other than the predetermined displacement angles.

The principal component analysis can derive an average value vector as a result of the analysis. Such average value vector can be used to estimate the reflectance more precisely at a displacement angle other than the predetermined displacement angles.

(5) The reflectance estimating method described in (3) or (4) includes a step of entering a reflectance of an object to be estimated, determining the aforementioned coefficient relating to the reflectance of such object to be estimated based on the aforementioned basic equation, constructing the basic equation by the determined coefficient and determining the reflectance of the object to be estimated based on the constructed basic equation.

By determining a basic equation including the eigenvector by the principal component analysis on the reflectance, the reflectance at an arbitrary displacement angle can be estimated from such basic equation. Therefore, a reflectance of an object to be estimated is entered and a coefficient relating to the reflectance of the object to be estimated is determined from the basic equation.

In this manner, it is rendered possible to construct, by the determined coefficient, a basic equation on the reflectance of the subject to be estimated. From this constructed basic equation, there can be determined a reflectance of the object to be estimated, other than the entered reflectance.

(6) The reflectance estimating method described in any of (1) to (5) includes a step of determining, with respect to the principal component vector obtained as a result of the principal component analysis, characteristics for each factor of the principal component vector with regards to the relationship between the principal component and the displacement angle, a step of determining a displacement angle corresponding to each of the feature points of the determined characteristics, and a step of estimating the reflectance at a displacement angle other than the predetermined displacement angles, based on thus determined displacement angle.

The principal component vector obtained by the principal component analysis can be represented by a polynomial, namely from a first principal component vector to an n-th principal component vector with a successively increasing ordinal number of terms. The amount of data to be used increases if all these principal component vectors are adopted. Also the rate of contribution thereof becomes lower as the number of terms of the principal component vectors increases. All the principal component vectors are therefore unnecessary and the principal component vectors of a certain number are sufficient for estimating the reflectance.

Therefore, with respect to the principal component vectors obtained as a result of the principal component analysis, the characteristics of the relationship between the principal component and the displacement angle are determined for each term of the principal component vectors. In such case, by determining the contribution factor, it is possible to determine the number of terms of the principal component vectors within a predetermined contribution factor.

Then a displacement angle is determined corresponding to each of the feature points of thus determined characteristics. The feature point of the characteristics of the principal component vector best represents the feature of the principal component vector, and the displacement angle of such feature point best represents the feature of the principal component vector. Therefore, by estimating the reflectance at a displacement angle other than the aforementioned predetermined displacement angles based on thus determined displacement angle, the estimation of the reflectance can be achieved effectively with a limited data amount.

(7) The reflectance estimating method described in (6) includes a step of forming a correspondence between a reflectance distribution of an arbitrary displacement angle and a luminocity (brightness) including relative luminous efficiency characteristics, and adopting a feature point of characteristics of each of the terms of the principal component vector obtained by the principal component analysis, as a displacement angle to be used.

The reflectance varies depending on the wavelength of the light. Therefore, the reflectance has to be determined in plural wavelengths.

Based on a consideration that the reflectance varying according to the wavelength of the light concerns a visible light to be observed by human eyes and that the visual sensitivity has a significant influence in the visual observation of such light, the present inventor has obtained a knowledge that the concept of reflectance can be replaced by a concept of lumonicity in the visual sensitivity, according to plural wavelengths.

Therefore, by forming a correspondence between a reflectance distribution of an arbitrary displacement angle and a luminocity including relative luminous efficiency characteristics, and adopting a feature point of characteristics of each of the terms of the principal component vector obtained by the principal component analysis, as a displacement angle to be used, it is rendered possible to obtain the eigenvector and the eigenvalue including the features of the entire wavelengths and to determine the reflectances of plural wavelengths from data of a single wavelength.

(8) In the reflectance estimating method described in (6) or (7), the displacement angle is plural angles.

In investigating a large number of eigenvectors and eignvalues obtained in the principal component analysis, the present inventor has obtained a result that at least two displacement angles are effective as the displacement angle of a feature point best representing the feature of the principal component vector. Also there has been a result that the number of the most preferred displacement angles is five and that such five displacement angles have an order of priority in terms of effectiveness.

The displacement angles are those determined by the principal component vectors up to a predetermined number of terms, for example the displacement angles determined by the respective principal component vectors up to the fourth one. There may be employed displacement angles determined by the principal component vectors up to an ordinal number of terms beyond the 4th term, but a preferred principal component vector is up to a 4th principal component vector.

In such case, the effectiveness is higher in the first principal component vector, and becomes gradually lower from the second principal component vector. Therefore, by employing two or more displacement angles starting from the displacement angle of the feature point best representing the feature of the first principal component vector, it is possible to easily and effectively estimate the reflectance at a displacement angle other than the predetermined displacement angles.

(9) In the reflectance estimating method described in (8), the aforementioned plural displacement angles are at least two angles among about 10°, about 16°, about 26°, about 38° and about 90°.

The five displacement angles optimum as the displacement angle for the feature points best representing the feature of the principal component vector are found as about 10°, about 16°, about 26°, about 38° and about 90°. Among these angles, effective combinations of the angles are, firstly angles of about 10° and about 90°, secondly an angle of about 26°, and thirdly angles of about 16° and about 38°, in the order of priority in terms of effectiveness.

Therefore, in case of adopting two displacement angles as the plural angles, there can be employed two angles of about 10° and about 90°; in case of adopting three displacement angles, there can be employed three angles of about 10°, about 90° and about 26°; in case of adopting four displacement angles, there can be employed four angles of about 10°, about 90°, about 26° and about 16°, or of about 10°, about 90°, about 26° and about 38°; and in case of adopting five displacement angles, there can be employed five angles of about 10°, about 90°, about 26°, about 16° and about 38°.

(10) In the reflectance estimating method described in any of (1) to (9), the estimation of the reflectance is made for a displacement angle of about 10° or larger.

Though it is most preferable that the reflectance can be derived at any arbitrary displacement angle, the reflectance in the vicinity of a displacement angle of 0°, namely in the vicinity of the normal reflecting direction may be unreliable as the data obtained by the actual measurement are unstable or excessively large. For this reason, such data, if employed in estimating the reflectance in the vicinity of the normal reflecting direction, may lead to a result poor in accuracy. Consequently, the aforementioned estimation of the reflectance utilizing the principal component analysis is executed for a displacement angle of about 10° or larger. In this manner there is obtained an estimated reflectance of a high precision.

(11) The reflectance estimating method described in (10) includes a step, after the aforementioned estimation of the reflectance, of estimating the reflectance for a displacement angle less than 10° by a multi-regression analysis utilizing three displacement angles of about 10° or larger.

For an image display, in addition to the estimation of the reflectance for the displacement angle of about 10° or larger, there is required the estimation of the reflectance in the vicinity of the normal reflecting direction, in order to maintain the continuity in the image. Therefore, the estimation of the reflectance for the displacement angle less than about 10°, namely in the vicinity of the normal reflecting direction, utilizing the data of the displacement angle employed in the aforementioned determination of the reflectance based on the principal component analysis, for the displacement angle of about 10° or larger.

In such manner, there can be obtained the reflectance which varies smoothly without a rapid variation over a displacement angle less than about 10° to a displacement angle of about 10° or larger. The multiple-regression analysis is preferably employed in the estimation in such case, but an interpolation analysis or a time-sequential analysis may also be employed.

(12) The reflectance estimating method described in (10) or (11) includes a step, after the aforementioned estimation of the reflectance, of estimating the reflectance for a displacement angle in excess of 90° by a multi-regression analysis utilizing three displacement angles of about 10° or larger but less than about 90°.

In order to maintain the continuity of an image in case of an image display, there is also required the estimation of the reflectance in a light emergent side, namely in a recurrent reflecting direction. Therefore, the estimation of the reflectance for a displacement angle exceeding about 90°, namely in the light emergent side or in the recurrent reflecting direction, is estimated by utilizing the data of the displacement angle employed in the aforementioned determination of the reflectance based on the principal component analysis, for the displacement angle of about 10° or larger but less than about 90°.

In such manner, there can be obtained the reflectance which varies smoothly without a rapid variation in a displacement angle exceeding about 90°. The multiple-regression analysis is preferably employed in the estimation in such case, but an interpolation analysis, an extrapolation process of the principal component vector, or a time-sequential analysis may also be employed.

(13) In the reflectance estimating method described in (11) or (12), the aforementioned three displacement angles are about 10°, about 26° and about 38°.

As the displacement angles for the feature points best representing the feature of the principal component vector employed in estimating the reflectance of a displacement angle, three angles of about 10°, about 26° and about 38° are found preferable.

(14) A reflectance estimating method for estimating a reflectance at an arbitrary displacement angle $\alpha$ which is an angle representing displacement from a normal light reflecting direction of an object, the method including (a) a step of executing a principal component analysis on reflectances of predetermined plural displacement angles within a predetermined angular range, (b) a step of selecting a principal component vector and a principal component obtained by the principal component analysis respectively as an eigenvector b and an eigenvalue, and determining characteristics of the eigenvector on the relationship between the eigenvalue and the displacement angle, (c) a step of determining a representative displacement angle from the determined characteristics, (d) a step of predetermining a basic equation on the reflectance, represented by the eigenvalue, the eigenvector and a coefficient to be multiplied on the eigenvector, (e) a step of determining the coefficient based on the basic equation, the representative displacement angle and the reflectance at the representative displacement angle and defining the basic equation utilizing the determined coefficient and the eigenvector as a calculation equation, (f) a step of estimating a reflectance at a displacement angle other than the aforementioned predetermined displacement angles within the aforementioned predetermined angular range based on the calculation equation, and (g) a step of estimating a reflectance of a displacement angle outside the aforementioned predetermined angular range by extrapolating the eigenvector.

The reflectance estimating method of the invention estimates a reflectance at an arbitrary displacement angle.

At first, a principal component analysis is executed on reflectances at predetermined plural displacement angles within a predetermined angular range, for example from about 10° to about 90°. A principal component vector, obtained as a result of the principal component analysis and representing the feature of the reflectance for the displacement angle, is taken as an eigenvector, also a principal component is taken as an eigenvalue, and characteristics of the eigenvector are determined on the relationship between the eigenvalue and the displacement angle.

A representative displacement angle is determined from the obtained characteristics, then a basic equation on the reflectance, represented by the eigenvalue, the eigenvector and a coefficient to be multiplied on the eigenvector, is determined in advance, and the coefficient is determined based on such basic equation, the representative displacement angle and the reflectance at the representative displacement angle. The basic equation utilizing the determined coefficient and the eigenvector is defined as a calculation equation, and a reflectance at a displacement angle other than the predetermined displacement angles is estimated in the predetermined angular range, utilizing such calculation equation.

Also for a displacement angle outside the predetermined angular range, the reflectance is estimated by extrapolating the eigenvector.

In this manner it is rendered possible to estimate the reflectance at an arbitrary displacement angle other than the predetermined displacement angles.

BRIEF DESCRIPTION OF THE DRAWINGS

FIGS. 8A to 8E are characteristic charts respectively showing first to fifth principal component vectors obtained as a result of a principal component analysis, wherein FIG. 8A shows a first principal component vector, FIG. 8B shows a second principal component vector, FIG. 8C shows a third principal component vector, FIG. 8D shows a fourth principal component vector and FIG. 8E shows a fifth principal component vector;

DETAILED DESCRIPTION OF THE PREFERRED EMBODIMENTS

In the following, an embodiment of the present invention will be explained in detail with reference to the accompanying drawings. In the present embodiment, the invention is applied to the estimation of a reflectance which is advantageously employable, for example in an image output of an automobile, in designing an object having a color such as an external paint color (external panel color) of the automobile.

First Embodiment

For example in computer graphics (CG) image output of an automobile, in order to improve the realistic feeling and to exactly represent an object such as an automobile, a reflectance of the object is measured and the color of the object is reproduced by such reflectance.

In the embodiment of the present invention, reflectance is considered as a physical amount for reproducing the object color, and spectral reflectance of the surface of the object is employed. Since the spectral reflectance may be given in different values depending on a light receiving direction of a measuring instrument, in a sample of a complex shape such as fibers or a metallic painted surface, the present embodiment employs, as the spectral reflectance, a spectral steric angle reflectance (hereinafter simply called reflectance) obtained by displacing a light incident angle to the object and a light receiving angle of a light receiving element which receives the light reflected by the object. However the present invention is not limited to the spectral steric angle reflectance but may simply employ a reflectance.

Figure 2:
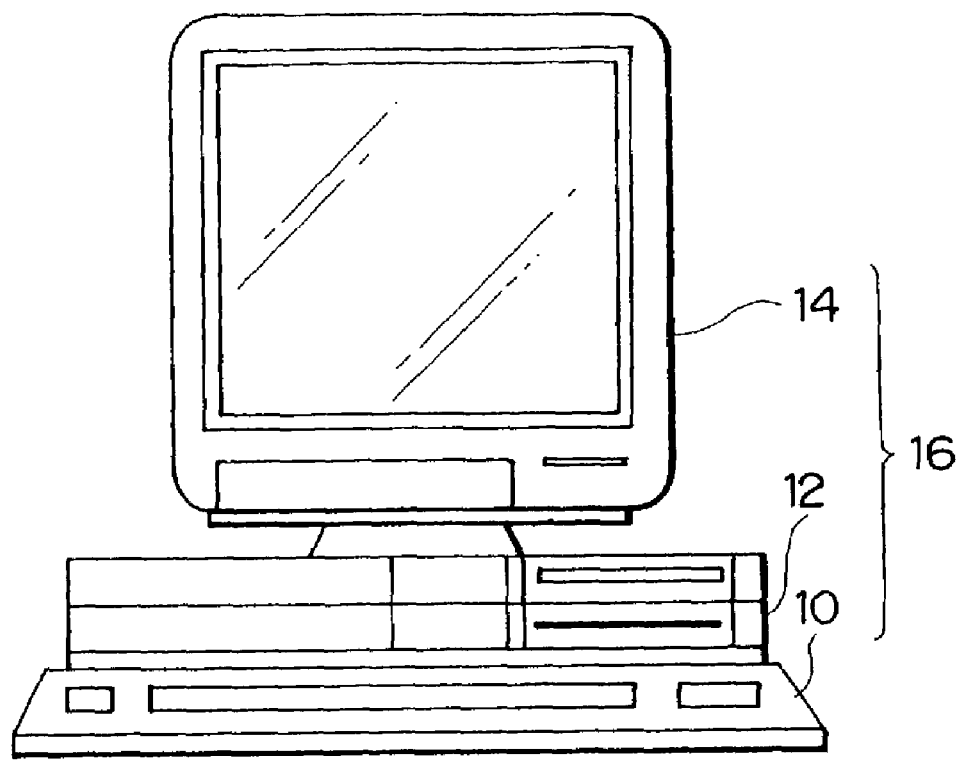
FIG. 2 is a schematic view showing the configuration of a reflectance estimating apparatus including a personal computer, for estimating the reflectance for use in CG.

As shown in FIG. 2, a reflectance estimating apparatus for CG of the present embodiment is provided with a personal computer 16. The personal computer 16 includes a keyboard 10 for entering color data or the like, a computer main body 12 for processing related data in order to estimate the desired reflectance according to a program stored in advance, and a CRT 14 for displaying the reflectance or the like obtained by processing in the computer main body 12. The computer main body 12 includes a CPU, a ROM and a RAM, and also has a memory for storing data such as a reflectance to be explained later.

At first the outline of the invention will be explained. The reflectance of an object varies depending on an arbitrary displacement angle, but the present inventor has obtained a knowledge that a principal component analysis on reflectances at predetermined plural displacement angles provides a feature on the reflectance, and the reflectances at plural displacement angles can be estimated from such feature amount. Stated differently, a principal component vector obtained by the principal component analysis represents the feature of the reflectance at a displacement angle, and the present embodiment utilizes an eigenvector which is the principal component vector obtained as a result of the principal component analysis, thereby estimating a reflectance at a displacement angle other than the predetermined displacement angles. In the following there will be given a detailed explanation on the principle of the invention and the estimation of the reflectance.

[Principle of Principal Component Analysis]

In the following, it will be explained that a vector X can be reconstructed by a vector p obtained in the principal component analysis, an eigenvector b, and a coefficient k.

At first, data to be analyzed are represented by a real vector X of an order p. Such real vector X is random, and an expected value E is defined by a following equation (1) utilizing the vector $\mu$:

$$E[X]=\mu \quad (1)$$

By defining a provisional vector $X'=X-\mu$, the equation (1) can be rewritten as (2):

$$E[X']=0 \quad (2)$$

Also by assuming the provisional vector X' as a real vector X, there is obtained a following equation (3):

$$E[X]=0 \quad (3)$$

In the following description, the provisional vector X' is assumed as the real vector X, as indicated in the equation (3).

Figure 3:
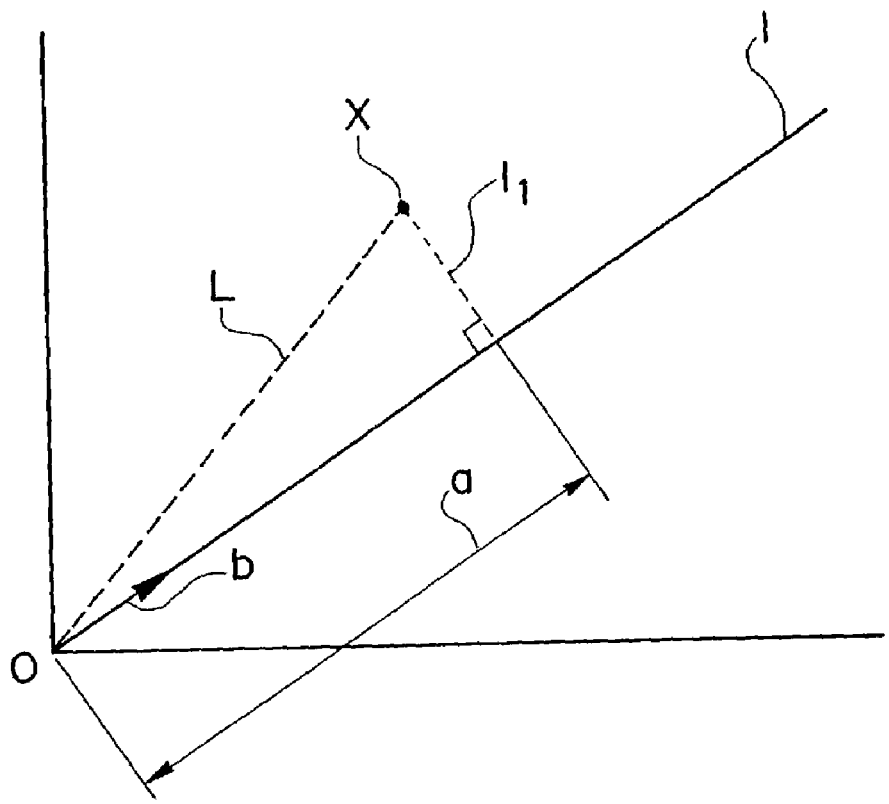
FIG. 3 is a schematic view for explaining a principal component analysis.

Now referring to FIG. 3, with respect to a line 1 extending in a direction of a unit vector b from the original point 0, a distance $1_1$ from a vector X to the line 1 can be represented by a following equation (4):

$$1_1 = (L^2 - a^2)^{1/2} \quad (4)$$

As the distance L from the original point 0 to the vector X is constant, the distance $1_1$ can be minimized by maximizing the distance a.

Since the unit vector b has a value |b|=1, the distance $1_1$ can be represented by a following equation (5):

$$1_1 = X^T \cdot b = b^T \cdot X \quad (5)$$

wherein $X^T$ is a transposed vector of the vector X. By defining the vector X and the transposed vector $b^T$ by following equations (6) and (7), the distance a can be represented by an equation (8):

$$X = (x_1, x_2, \ldots, x_p) \quad (6)$$

$$b^T = (b_1, b_2, \ldots, b_p) \quad (7)$$

$$a = X^T b = b^T X$$

$$= b_1 x_1 + b_2 b_2 + \ldots + b_p x_p \quad (8)$$

An expected value E[a] and a dispersion $E[a^2]$ of the distance a can be represented by following equations (9) and (10):

$$\text{Expected value } E[a] = E[X^T b] = E[X^T]b \quad (9)$$

$$\text{Dispersion } E[a^2] = E[aa^T] = E[b^T X X^T b] \quad (10)$$
$$= bE[XX^T]b = b^T R b$$

wherein R is a co-dispersion matrix of the vector X and is a real object matrix.

Thus the eigenvalues are all positive or 0. The dispersion, being a function of the unit vector b, can be represented by a following equation (11):

$$\Psi(b) = b^T R b = \rho^2 \quad (11)$$

The unit vector b which has an extreme value of the dispersion $\Psi(b)$ in the equation (11) is an eigenvector of the co-dispersion matrix R. Such eigenvector will be explained in the following.

The distance L is determined from a following equation (12), utilizing Lagrange's method of undetermined multipliers, and the equation (12) is differentiated with b as shown in (13), which is then assumed to be equal to 0, whereby an equation (14) is obtained:

$$L = b^T R b + 1(1 - b^T b) \quad (12)$$

$$(\partial L / \partial b) = 2Rb - 2lb = 0 \quad (13)$$

$$Rb = lb \quad (14)$$

A constant 1 satisfying the equation (14) is an eigenvalue, and the unit vector b is an eigenvector corresponding to the eigenvalue.

Eigenvalue: $[1_1, 1_2, \ldots, 1_p]$

Eigenvector: $[b_1, b_2, \ldots, b_p] \quad (15)$

Representing the eigenvalue of the co-dispersion matrix R by $\{1_1, 1_2, \ldots, 1_p\}$ (wherein $1_1 > 1_2 > \ldots > 1_p$), the equation (14) can be represented by a following equation (16):

$$Rb_j = 1_j b_j, j=1, 2, \ldots, p \quad (16)$$

Then, by defining a set $[b_1, b_2, \ldots, b_p]$ of the unit vector b by a following equation (17), there stands an equation (18):

$$U = [b_1, b_2, \ldots, b_p] \quad (17)$$

$$RU = UA \quad (18)$$

wherein:

$$\Lambda = \begin{bmatrix} l_1 & & & 0 \\ & l_2 & & \\ & & \ddots & \\ 0 & & & l_p \end{bmatrix} \quad (19)$$

U is a normal orthogonal matrix which provides a following equation (20), and an equation (21) stands:

$$U^T U = I \quad (20)$$

$$U^{-1} = U^T \quad (21)$$

wherein I represents a unit matrix.

Thus, there stand following equations (22) and (23):

$$U^T R U = \Lambda \quad (22)$$

$$\Psi(b_i) b_i^T R b_i = b^T 1_i b_i = 1_i \quad (23)$$

Therefore, there stands a relation of a following equation (24):

$$\Psi(b_1) > \Psi(b_2) > \ldots > \Psi(b_p) \quad (24)$$

By representing the vector X with bases $b_1$, $b_2$, $b_p$, a projection $k_j$ on a base $b_j$ of the vector X can be represented by a following equation (25):

$$k_j = b_j^T X = X^T b_j \quad (25)$$

wherein j=1, 2, . . . , p

The equation (25) can be developed into following presentation:

$$k_1 = b_2^T X$$

$$k_2 = b_2^T X$$

$$k_p = b_p^T X$$

or a matrix presentation shown in (26):

$$\begin{bmatrix} k_1 \\ k_2 \\ \vdots \\ k_p \end{bmatrix} = \begin{bmatrix} b_1^T \\ b_2^T \\ \vdots \\ b_p^T \end{bmatrix} X = [b_1 b_2 \ldots b_p]^T X \quad (26)$$

Consequently, as shown in (27), the vector k can be obtained by a multiplication of the transposed matrix U and the vector X:

$$k = U^T X \quad (27)$$

By representing the equation (27) by the vector X in a polynomial format, following equations (28) and (29) are obtained:

$$X = Uk = [b_1 b_2 \ldots b_p] \begin{bmatrix} k_1 \\ k_2 \\ \vdots \\ k_p \end{bmatrix} \quad (28)$$

$$= k_1 b_1 + k_2 b_2 + \ldots + k_p b_p \quad (29)$$

In this manner, the vector X can be reconstructed with the eigenvector $\{b_1, b_2, \ldots, b_p\}$.

The vector X, being in fact the provisional vector X', is returned to the original form by the equations (1) and (2) to obtain a following equation (32):

$$X = \mu + k_1 b_1 + k_2 b_2 + \ldots + k_p b_p \quad (32)$$

wherein $$k_i = b_i^T X = X^T b_i \quad (33)$$

I=1, 2, . . . , p

Consequently, the vector X can be reconstructed by the vector μ, the eigenvector $\{b_1, b_2, \ldots, b_p\}$ and the coefficient $\{k_1, k_2, \ldots, k_p\}$.

[Error]

In the foregoing explanation, the eigenvector $\{b_1, b_2, \ldots, b_p\}$ of a multiple order is employed but the amount of data increases in such method. In the following there will be explained a method of reducing the number of order without decreasing the information amount.

A lower number of order can be realized without a significant decrease in the information amount, by leaving, among the p orthogonal axes of the eigenvector $\{b_1, b_2, \ldots, b_p\}$, axes showing large dispersions and deleting axes showing small dispersions.

The equation (32) representing the vector X can be written as a following equation (34):

$$X = \mu + \sum_{j=1}^{p} k_j b_j \quad (34)$$

In this equation, m axes (m<p) are selected in the descending order of the engenvalue, and a new vector *X constituted by the selected m eigenvalues is represented by a following formula (35):

$$*X = \mu + \sum_{j=1}^{m} k_j b_j \quad (35)$$

An error e in such a representation is X−*X, and can be represented by a following equation (36):

$$e^T * X = \sum_{i=m+1}^{p} k_i b_i^T \cdot \sum_{i=1}^{m} k_j b_j \quad (36)$$

$$= \sum_{j=m+1}^{p} \sum_{j=1}^{m} k_i k_j b_i^T b_j$$

$$= 0$$

The error e is orthogonal to the vector *X, and this fact is called a principle of orthogonality. Thus a lower number of order can be realized without significantly losing the information amount, by leaving the axes of larger dispersions among the p orthogonal axes of the eigenvector b and deleting the axes of smaller dispersions.

[Principle of Reflectance Estimation]

In the following there will be explained a principle of reflectance estimation by the principal component analysis, based on the principle of the principal component analysis explained in the foregoing.

Figure 4:
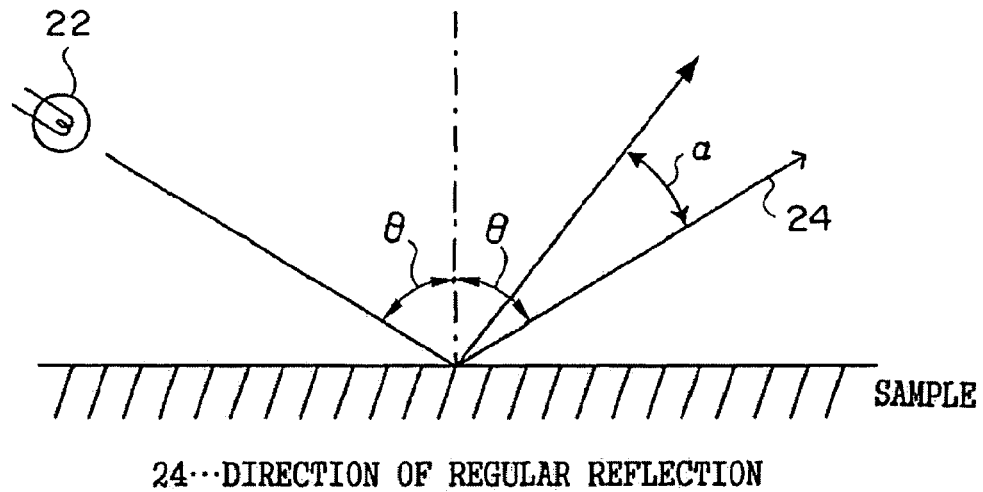
FIG. 4 is a schematic view for explaining a displacement angle.

Reflective characteristics of an object (sample) are measured under a condition shown in FIG. 4. Referring to FIG. 4, a light source 22 has an incident angle θ, and a direction 24 of a reflective angle which is the same as the incident angle is called a normal reflecting direction. An angle representing displacement from the normal reflecting direction 24 toward a normal line is represented by a displacement angle α.

Figure 5:
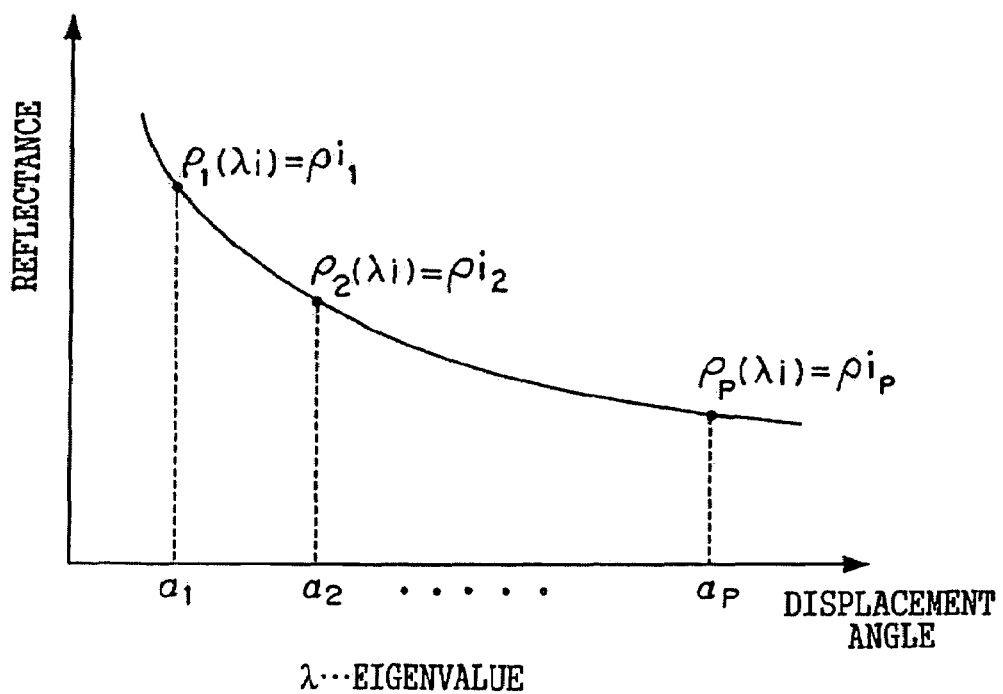
FIG. 5 is a characteristic chart showing the relationship between a displacement angle α and a reflectance.

FIG. 5 is a characteristic chart showing a relationship between the displacement angle α and the reflectance. As the reflectance varies by a wavelength λ, a reflectance at an arbitrary wavelength λ and at a displacement angle $\{\alpha_1, \alpha_2, \ldots, \alpha_p\}$ is represented by $\{\rho_1, \rho_2, \ldots, \rho_p\}$.

At first, a reflectance at an arbitrary wavelength $\lambda_i$ and at a displacement angle $\{\alpha_1, \alpha_2, \ldots, \alpha_p\}$ is represented by a vector X of a following equation (38):

$$X^i = \{\rho^i_1, \rho^i_2, \rho^i_p\}^T \tag{38}$$

Also among reflectance data of the displacement angle $\{\alpha_1, \alpha_2, \ldots, \alpha_p\}$ for N wavelengths $\lambda_i$, a j-th sample (reflectance data) of a j-th vector $X(j=1, 2, \ldots, N)$ is defined by a following equation (39):

$$X^i_j = \{\rho^i_{1j}, \rho^i_{2j}, \ldots, \rho^i_{pj}\}^T \tag{39}$$

Following description will be concentrated on a wavelength $\lambda_i$.

By employing the eigenvalue 1 and the eigenvector b, obtained as explained by the principle of the principal component analysis, as shown in the foregoing equation (15), and defining the eigenvector b by a following equation (40), an equation (41) can be derived from the equation (32):

$$b^i_j = \{b^i_{1j}, b^i_{2j}, \ldots, b^i_{pj}\}^T \tag{40}$$

$$X^i_j = \mu^i + k^i_{1j} b^i_1 + k^i_{2j} b^i_1 + \ldots + k^i_{pj} b^i_p \tag{41}$$

Following table shows a relationship between a sample and reflectances corresponding to displacement angles.

TABLE 1

| Sample | Displacement angle | | | |
|---|---|---|---|---|
| | $\alpha_1$ | $\alpha_2$ | ... | $\alpha_p$ |
| 1 | $\rho^i_{11}$ | $\rho^i_{21}$ | ... | $\rho^i_{p1}$ |
| 2 | $\rho^i_{12}$ | $\rho^i_{22}$ | ... | $\rho^i_{p2}$ |
| . | . | . | . | . |
| . | . | . | . | . |
| . | . | . | . | . |
| N | $\rho^i_{1N}$ | $\rho^i_{2N}$ | . | $\rho^i_{pN}$ |
| . | | | | |
| . | | | | |
| Average μ | $\mu_1$ | $\mu_2$ | . | $\mu_N$ |
| . | | | | |
| . | | | | |

The vector μ is an average vector which can be represented by a following equation (42):

$$\mu^i = \{\mu^i_1, \mu^i_2, \ldots, \mu^i_p\}^T \tag{42}$$

wherein:

$$\mu^i_v = \frac{1}{N}\sum_{m=1}^{N} \rho^i_v m \tag{43}$$

Also the eigenvalue 1 $\{1_1, 1_2, \ldots, 1_p\}$ and the eigenvector $b^i_j = \{b^i_{1j}, b^i_{2j}, \ldots, b^i_{2j}\}^T$ satisfy a following equation (45):

$$R^i b^i_j = 1^i_j b^i_j \tag{45}$$

wherein j=1, 2, ..., p and:

$$R^i = E[X\,X^T] = \begin{bmatrix} C^i_{11} & C^i_{12} & \cdots & C^i_{1p} \\ C^i_{21} & C^i_{22} & \cdots & C^i_{2p} \\ \vdots & \vdots & \ddots & \vdots \\ C^i_{p1} & C^i_{p2} & \cdots & C^i_{pp} \end{bmatrix}$$

$$C^i_{kj} = \frac{1}{N-1}\sum_{m=1}^{N} [\rho^i_{nk} - \mu^i_k][\rho^i_{nj} - \mu^i_j]$$

$$k^i_{ij} = b^{iT}_i X^i_j$$

The equation (41) in vector representation can be rewritten as (49) in element representation:

$$\begin{bmatrix} \rho^i_{1j} \\ \rho^i_{2j} \\ \vdots \\ \rho^i_{pj} \end{bmatrix} = \begin{bmatrix} \mu^i_1 \\ \mu^i_2 \\ \vdots \\ \mu^i_p \end{bmatrix} + k^i_{1j}\begin{bmatrix} b^i_{11} \\ b^i_{21} \\ \vdots \\ b^i_{p1} \end{bmatrix} + k^i_{2j}\begin{bmatrix} b^i_{12} \\ b^i_{22} \\ \vdots \\ b^i_{p2} \end{bmatrix} + \ldots + k^i_{pj}\begin{bmatrix} b^i_{1p} \\ b^i_{2p} \\ \vdots \\ b^i_{pp} \end{bmatrix} \tag{49}$$

Among the first to p-th principal component vectors in the equation (49), the first to m-th principal component vectors are used to obtain a following equation (50):

$$\begin{bmatrix} \rho^i_{1j} \\ \rho^i_{2j} \\ \vdots \\ \rho^i_{pj} \end{bmatrix} = \begin{bmatrix} \mu^i_1 \\ \mu^i_2 \\ \vdots \\ \mu^i_p \end{bmatrix} + k^i_{1j}\begin{bmatrix} b^i_{11} \\ b^i_{21} \\ \vdots \\ b^i_{p1} \end{bmatrix} + k^i_{2j}\begin{bmatrix} b^i_{12} \\ b^i_{22} \\ \vdots \\ b^i_{p2} \end{bmatrix} + \ldots + k^i_{mj}\begin{bmatrix} b^i_{1m} \\ b^i_{2m} \\ \vdots \\ b^i_{pm} \end{bmatrix} \tag{50}$$

As will be understood from this equation, the reflectance ρ at an arbitrary displacement angle α can be represented by the average vector μ, the eigenvector b and the coefficient k. Consequently, by determining the coefficient k from a known reflectance measured on the object, the reflectance at a displacement angle other than the reflectances at the known displacement angles can be derived from this equation. This equation is solved for the coefficient k to obtain:

$$\begin{bmatrix} k_{ij} \\ k_{ij} \\ \vdots \\ k_{ij} \end{bmatrix} = \begin{bmatrix} b^i_{11} & b^i_{12} & \cdots & b^i_{1m} \\ b^i_{21} & b^i_{22} & \cdots & b^i_{2m} \\ \vdots & \vdots & \ddots & \vdots \\ b^i_{p1} & b^i_{p2} & \cdots & b^i_{pm} \end{bmatrix}^{-1} \begin{bmatrix} \rho^i_{1i} - \mu^i_1 \\ \rho^i_{2i} - \mu^i_2 \\ \vdots \\ \rho^i_{pi} - \mu^i_p \end{bmatrix}$$

In this case, however, since the wavelength is selected in advance, the determination of the reflectance is executed for all the wavelengths utilizing the wavelength $\lambda_i$.

[Estimation of Reflectance]

Now the function of the present embodiment will be explained according to the outline and the principle explained in the foregoing.

Figure 6:
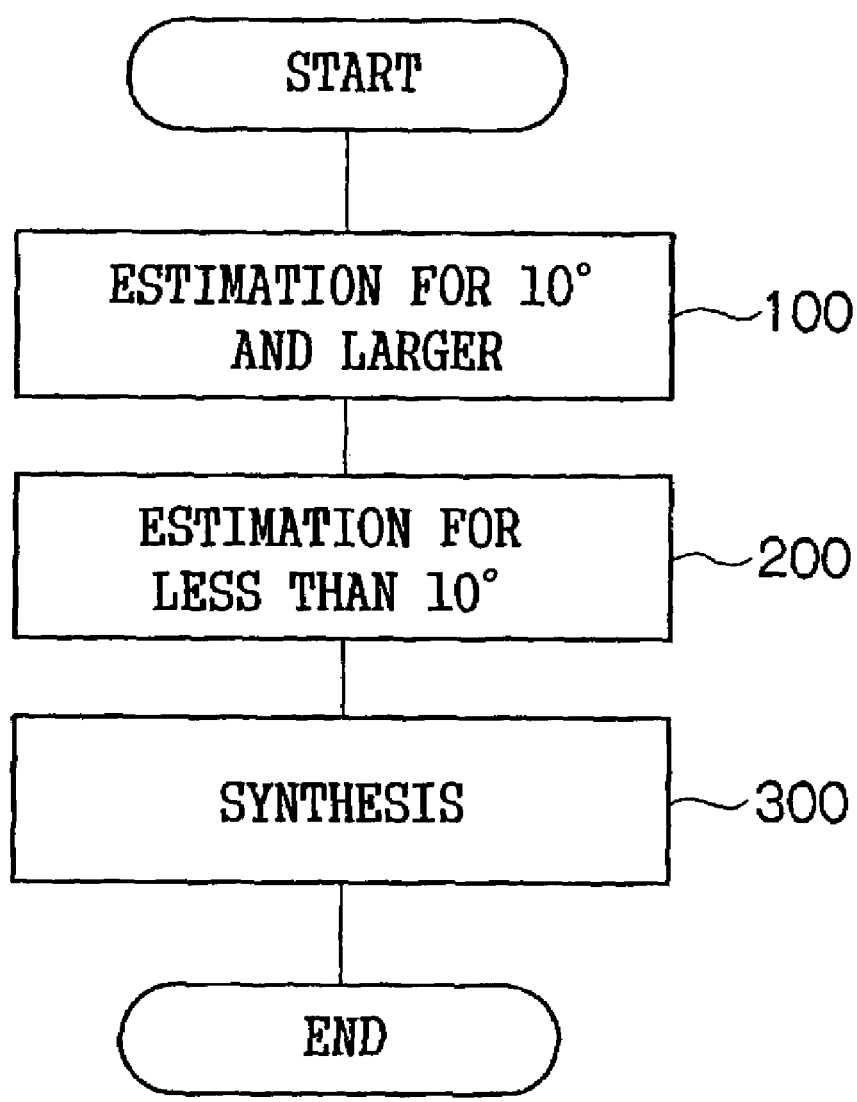
FIG. 6 is a flow chart showing the flow of a process for estimating reflectance of any displacement angle.

When the reflectance estimating apparatus for CG is powered and the personal computer 16 is activated, a processing routine shown in FIG. 6 is executed and the sequence proceeds to a step 100. A step 100 estimates the reflectance (for example spectral steric angle reflectance) for displacement angles of 10° or larger. A next step 200 estimates the reflectance for displacement angles less than 10°. Then a step 300 synthesizes the reflectances obtained in the steps 100 and 200, thereby deriving the reflectances for all the displacement angles, whereupon the present routine is terminated.

In the above-described process, the reflectance estimation is separated at a boundary of a displacement angle of 10° in order to improve the precision of the result of estimation, since the estimation of the reflectance at the normal reflecting direction 24 by the principal component analysis may provide unstable results for example because of a fluctuation in the light measurement data.

The present inventor has obtained an experimental result that a displacement angle of about 10° is a most preferred as an angle for obtaining the normal reflection data in the vicinity of the normal reflecting direction 24, i.e., at a displacement angle of 0°. This is because the principal component analysis of the aforementioned principle provides an unstable result of analysis if the boundary of the displacement angle is taken smaller than about 10°.

In the present embodiment, therefore, a boundary for the displacement angle is set at 10°, and different processes are executed for estimating the reflectance for a displacement angle less than 10° (estimation in the vicinity of the normal reflection), and for a displacement angle of 10° or larger (estimation for principal displacement angle). More specifically, the reflectance for a displacement angle of 10° or larger is estimated by the principal component analysis of the multi-variable analysis explained in the foregoing, and the reflectance for a displacement angle less than 10° is estimated by another estimation process. Examples of the estimation process for the displacement angle less than 10° include an insertion of measured data, a multiple regression analysis of multi-variable analysis and an interpolation process.

Figure 1:
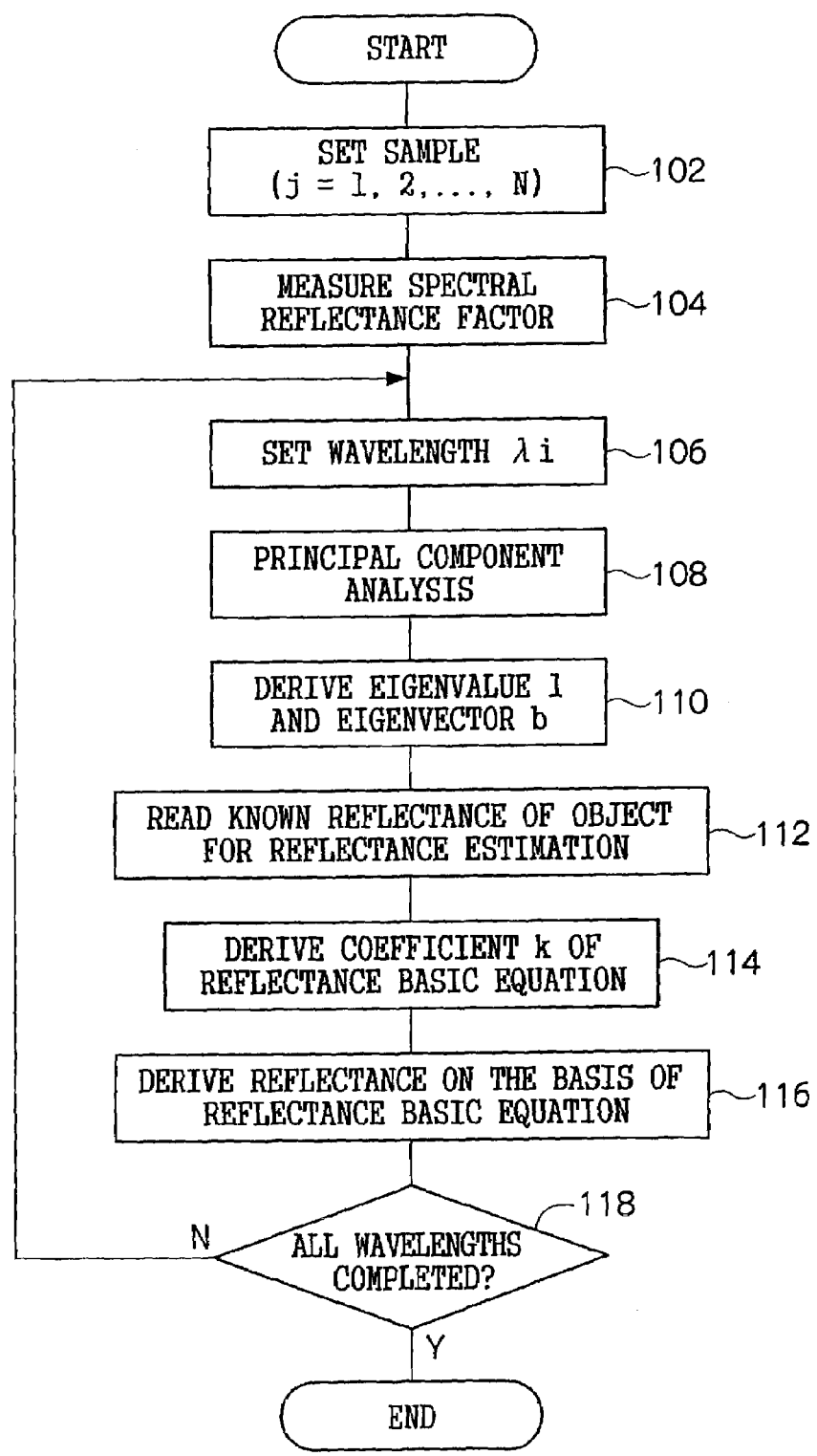
FIG. 1 is a flow chart showing the process flow of a reflectance estimating process by a principal component analysis in a first embodiment of the present invention.

In the following, details of the step 100 will be explained. In the reflectance estimation (principal displacement angle estimation) process of the step 100 for the displacement angle of 10° or larger, there is executed a process routine shown in FIG. 1.

A step 102 sets a sample (j=1, 2, . . . , N) for obtaining light measurement data, and a next step 104 measures the reflectance. The reflectance of each sample may be measured with a reflectance measuring device (for example a spectral reflectance factor measuring device), or may be obtained by reading data of measured values, or entered from a keyboard. A next step 106 sets an arbitrary wavelength $\lambda_i$ for fixing the wavelength $\lambda_i$ as explained in the foregoing principle of reflectance estimation. In this manner there can be obtained reflectance or light measurement data for a displacement angle at the arbitrary wavelength $\lambda_i$.

A next step 108 initiates a principal component analysis according to the foregoing principle, utilizing the light measurement data set in the step 106, and a step 110 derives an engenvalue 1 and an eigenvector b obtained by the principal component analysis. The step 110 also derives an average vector μ.

A next step 112 reads a known reflectance of the object of which reflectance is to be estimated. Number of the reflectance to be read in this step corresponds to the aforementioned variable m. Based on thus read known reflectances, a step 114 derives a coefficient k utilizing the coefficient-deriving equation explained in the foregoing. Thus, a basic equation for the reflectance, shown in (50), is determined. A next step 116 utilizes the basic equation determined in the step 114 to derive a reflectance at an arbitrary displacement angle. The reflectance derived in this step includes a reflectance of a displacement angle other than the displacement angles read in the step 112.

Then a step 118 discriminates whether the above-described process for the wavelength set in the step 106 has been completed for all the wavelengths, for example all the visible wavelength range (such as 400 to 700 nm), and, if not completed, the above-described process is executed in repetition, but, if completed, the present routine is terminated. The wavelength set in the step 106 is preferably set at wavelength values sufficient for color reproduction within the wavelength range to be utilized as the reflectance data, for example at every 10 nm.

In the following, details of the step 200 will be explained. In the present embodiment, the estimation of the reflectance for a displacement angle less than 100 in the step 200 (estimation in the vicinity of the normal reflection) is executed, for example, by an insertion of actually measured data. For example the reflectance is actually measured for each of displacement angles α=0°, 1°, 2°, . . . , 9°, and such measured data are employed as the reflectance.

The reflectances employing the measured data involve a certain error but can provide a more or less smooth curve. The measurement for obtaining the measured data is preferably executed at 10+5=15 displacement angles or measuring angles.

It is also possible to actually measure the reflectance of the sample at a displacement angle less than 10° and to execute a data interpolation so as to obtain a smooth continuity with the data at a displacement angle at 10° or larger. In this manner there can be obtained reflectances smoothly continuing over a displacement angle range from 0° to 90°.

As explained in the foregoing, the present embodiment allows to easily determine the reflectance of a displacement angle other than the reflectances of the displacement angles which are already known as measured data, by the basic equation for the reflectance derived from the eigenvector obtained from the principal component analysis, so that a desired reflectance can be obtained while reducing the amount of the measured data.

In the reflectance estimation for a displacement angle less than 10° in the step 200, reliability of the result is low even if measured values are faithfully reproduced since the result of measurement of the reflectance for a displacement angle less than 10° shows fluctuation with a large error. However, in an image display as in the CG, the image display itself cannot be realized unless data are prepared. For this reason, the reflectance data are indispensable also for the displacement angles less than 10°.

In such image display, emphasis may be given to a smooth continuity of the image display rather than to the reliability of the reflectance to be utilized. Specifically, an abrupt variation in the reflectance, if present when the displacement angle is changed continuous manner, may cause a flickering or a color jump in the image display at a displacement angle corresponding to such abrupt variation in the reflectance, thereby giving an uncomfortable feeling to the user.

It is therefore preferable to execute the reflectance estimation of smoothly continuous behavior, maintaining the behavior of the reflectance within a range from 10° to 90° which has been efficiently estimated as explained in the foregoing. For this reason, the present embodiment has explained a process of inserting actually measured data.

Second Embodiment

In the foregoing embodiment, the reflectance is processed for each wavelength $\lambda_i$. The present embodiment processes the reflectance not for each wavelength $\lambda_i$ but by grasping an entire feature for example over a wavelength range of the visible light. In the present embodiment, luminocity or brightness is employed for grasping the entire feature over the wavelength range. The present embodiment has a configuration approximately similar to that of the foregoing embodiment, wherein parts same as in the foregoing embodiment are represented by same symbols and omitted from the detailed description.

The present embodiment employs an incident angle of 60°, instead of 45° which is usually utilized as the incident angle θ. This is to enable the use of an angle 90° as a representative displacement angle to be determined from first to fifth principal component vectors, as will be explained in the following.

The present inventor has obtained a knowledge that a featuring displacement angle exists, by employing the luminocity for grasping the entire feature over the wavelength range. In the following there will be explained an outline and a principle of determination of such featuring displacement angle and estimation of the reflectance based on thus determined displacement angle.

[Determination of Representative Displacement Angle]

A color of an object can be determined from a spectral distribution (spectral radiation luminance) of an incident light to a human eye when looking at such object. The spectral radiation luminance $I(\lambda)$ can be determined from the light of a main light source, such as a solar light. A luminocity or brightness can be represented by considering visibility characteristics, called standard relative luminous efficiency $y(\lambda)$, in combination with the spectral radiation luminocity $I(\lambda)$.

Therefore, the present embodiment utilizes a luminocity Y represented by equations (51) and (52) instead of the reflectance $\rho^i_{kj}$ employed for example in the equation (50:)

$$\rho_{kj}=k\Sigma\rho^i_{ki}I(\lambda i)\overline{y}(\lambda i)\Delta\lambda \tag{51}$$

$$k=100/\Sigma I\ (\lambda i)\overline{y}(\lambda i)\Delta \tag{52}$$

wherein $I(\lambda)$ represents a spectral distribution of a light source, and $\overline{y}(\lambda_I)$ represents a relative luminous efficiency.

The luminocity Y defined in the equations (51), (52) is used for the aforementioned principal component analysis to obtain a principal component vector (eigenvector) and an eigenvalue. A feature found for each principal component vector in this analysis is understood to represent the entire feature over the wavelength range for each principal component vector.

Figure 7:
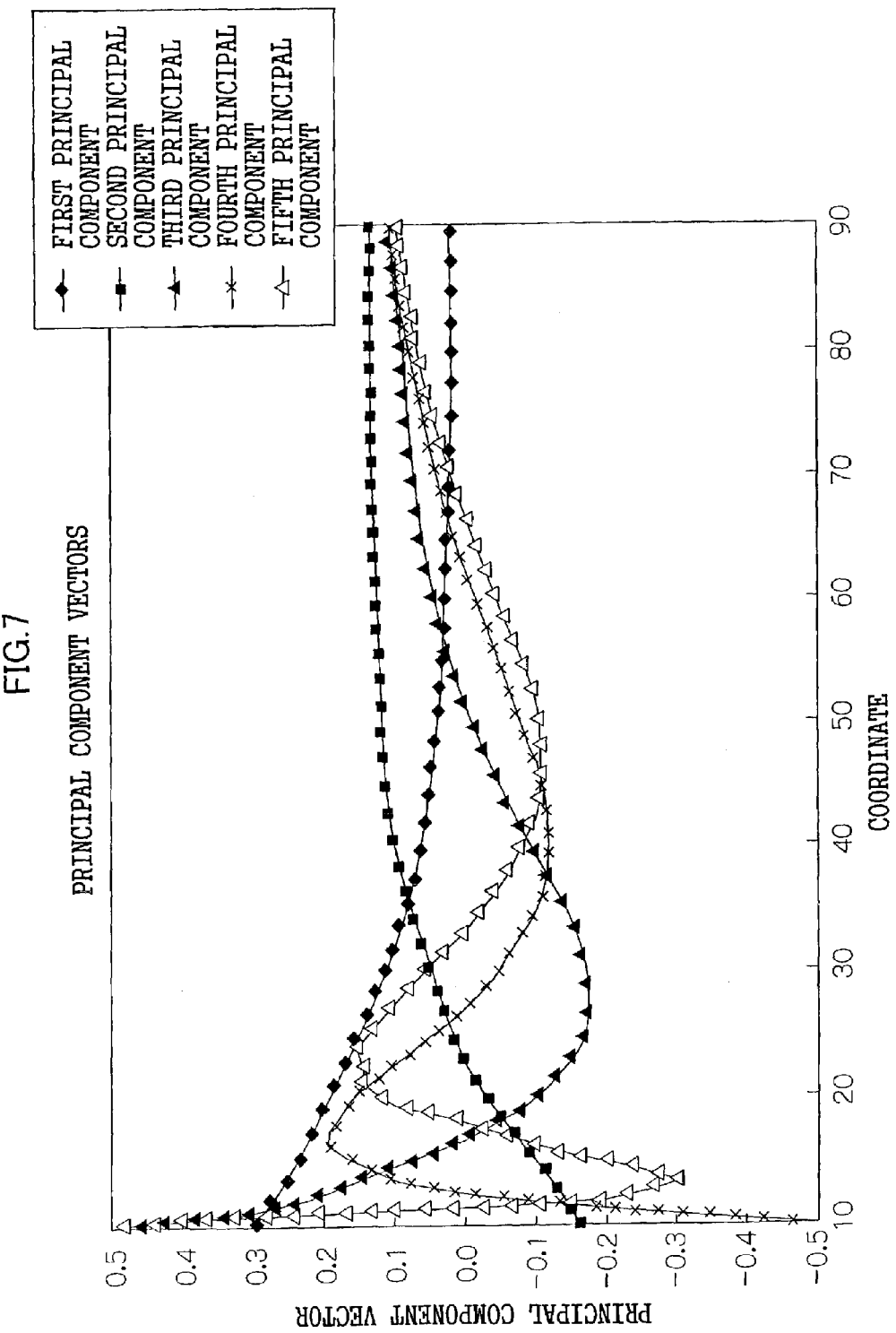
FIG. 7 is a characteristic chart showing first to fifth principal component vectors obtained as a result of a principal component analysis.

FIG. 7 shows first to fifth principal component vectors obtained as a result of the principal component analysis. Each of the principal component vectors (eigenvectors), from the first one to the fifth one obtained by the principal component analysis, as respectively shown in FIGS. 8A to 8E, has a feature point in the characteristics as a function of the displacement angle, different for each vector. In the present embodiment, the principal component vectors from the first one to the fifth one are considered, but it may also be applied to a sixth principal component vector or that of a higher order. The feature point means a displacement angle where the characteristics as a function of the displacement angle assumes a maximum value or a minimum value in each principal component vector (eigenvector).

Figure 8A:
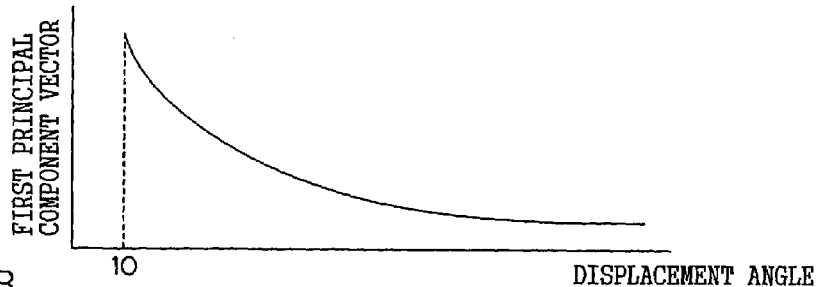
Figure 8B:
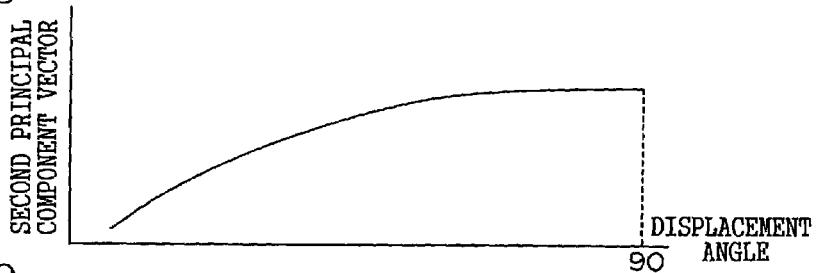
Figure 8C:
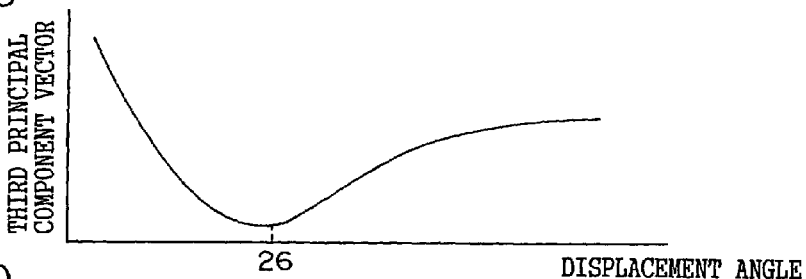
Figure 8D:
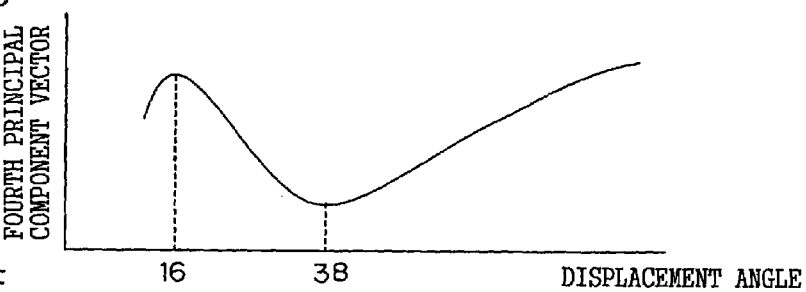
Figure 8E:
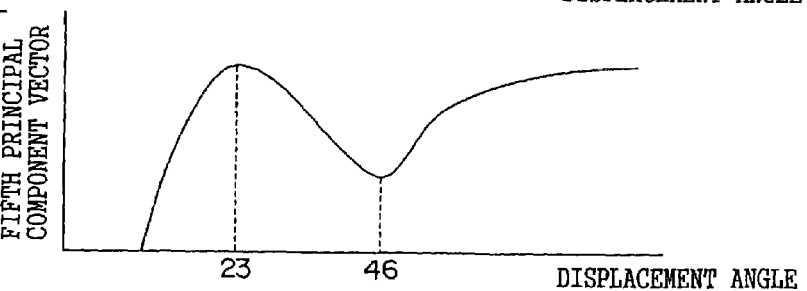

More specifically, the first principal component vector has monotonously decreasing characteristics in which the value gradually decreases as shown in FIG. 8A, and the feature point can be considered to exist at both ends, namely at 10° and 90°. The second principal component vector has monotonously increasing characteristics in which the value gradually increases as shown in FIG. 8B, and the feature point can be considered, as in the first principal component vector, to exist at both ends, namely at 10° and 90°. The third principal component vector is of characteristics having a single maximum value in which the value gradually increases to such maximum value and then gradually decreases thereafter as shown in FIG. 8C, and the feature point can be considered to exist at 26° corresponding to the maximum value. The fourth principal component vector is of characteristics having a single maximum value and a single minimum value in which the value gradually increases to such maximum value, then gradually decreases to such minimum value and gradually increases thereafter as shown in FIG. 8D, and the feature point can be considered to exist at 16° corresponding to the maximum value and at 380 corresponding to the minimum value. The fifth principal component vector is of characteristics having a single maximum value and a single minimum value, as in the fourth principal component vector, in which the value gradually increases to such maximum value, then gradually decreases to such minimum value and gradually increases thereafter as shown in FIG. 8E, and the feature point can be considered to exist at 23° corresponding to the maximum value and at 46° corresponding to the minimum value.

These results are summarized in Table 2

TABLE 2

Principal component vectors and displacement angles of feature points

| Principal component vector | first | second | third | fourth | fifth |
|---|---|---|---|---|---|
| Displacement angle at feature point (°) | 10 (90) | 90 (10) | 26 | 16 38 | 23 46 |

A feature point means a point where the graph assumes a greatest or least value or constitutes a maximum or minimum point.

By introducing a concept of a contribution factor of each principal component vector, results shown in Table 3 can be obtained.

TABLE 3

Principal component vectors and cumulative contribution factors

| Principal component vector | first | second | third | fourth | fifth |
|---|---|---|---|---|---|
| Eigenvalue | 95297.0946 | 12802.7688 | 1239.2417 | 59.2851726 | 14.9671726 |
| Contribution factor | 0.86799556 | 0.11987601 | 0.01123389 | 0.00063723 | 0.00016524 |
| Cumulative contribution factor | 0.86799556 | 0.98787157 | 0.99910546 | 0.99974269 | 0.99990793 |

As will be understood from this table, a cumulative contribution factor of 99.9% can be obtained with the principal component vectors down to the third principal component vector.

Therefore, the principal component vectors can be considered with a contribution factor of about 99% or higher by adopting the first and second principal component vectors, 99.9% or higher by adopting the first to third principal component vectors, 99.97% or higher by including the fourth principal component vector, and 99.99% or higher by including the fifth principal component vector. The present inventor has obtained a knowledge that the adoption up to the fifth principal component vector is sufficient for extracting the features. More specifically, the feature extraction can be achieved by considering down to the second principal component vector, preferably to the third principal component vector, more preferably to the fourth principal component vector and most preferably to the fifth principal component vector.

In consideration of a fact that, among the principal component vectors providing a cumulative contribution factor of 99.9% or higher, the cumulative contribution factor of 99.98% obtained including the fourth and that of 99.99% obtained including the fifth have little difference, the present inventor has obtained a knowledge that the adoption down to the fourth is sufficient for enabling the reflectance estimation with a smaller amount of data, and has thus reached following feature points. More specifically, the representative displacement angles are the feature points of the first to fourth principal component vectors and are following five displacement angles:

10°, 90°, 26°, 38° and 16°.

Thus, the displacement angles enabling to grasp the feature of the entire wavelength range are 10°, 16°, 26°, 38° and 90°. These five displacement angles are adopted in the following description.

The present inventor has also obtained an experimental result indicating that these five displacement angles {10°, 16°, 26°, 38° and 90°} are most effective and the precision is deteriorated even with a slight aberration for example by 1°. However, these displacement angles are anticipated to vary by an error in the measuring apparatus which defines the angle. Therefore, the values of these five displacement angles {10°, 16°, 26°, 38° and 90°} are not limited to such figures within an allowance of a measurement error. Also these values are still effective in a vicinity of these five displacement angles {10°, 16°, 26°, 38° and 90°} though the accuracy is deteriorated, and may therefore be effective for other displacement angles in the vicinity.

There is also obtained a result that these five displacement angles have different priorities according to the contribution factors thereof. More specifically, for grasping the feature of the entire wavelength range, the priority is highest in the displacement angles of 100 and 900, then in the displacement angle of 26°, and then the displacement angles of 16° and 38°. Therefore, a preferred utilization of the displacement angles is achieved by utilizing two or more displacement angles among five. For example, in case of using two displacement angles, it is preferred to use two displacement angles of 10° and 90°, and, in case of using three displacement angles, it is preferred to use three displacement angles of 10°, 90° and 26°. In case of using four displacement angles, it is preferred to use four displacement angles of 10°, 90°, 26° and 16°, or 10°, 90°, 26° and 38°.

[Principle of Reflectance Estimation: Displacement Angle of 10° or Larger]

In the following there will be explained the principle of reflectance estimation by a principal component analysis, based on the foregoing description of the principle of the principal component analysis and of the determination of the displacement angle.

By selecting displacement angles as α=10, 11, 12,..., 90 (°), the aforementioned variable p becomes p=81. As the representative displacement angles, the above-explained displacement angles α=10, 16, 26, 38 and 90 are employed. The foregoing equation (50) is rewritten for the five displacement angles a to obtain a following equation (54), which is rewritten for the coefficient k to obtain a following equation (55):

$$\begin{bmatrix} \rho_1^i \\ \rho_2^i \\ \vdots \\ \rho_5^i \end{bmatrix} = \begin{bmatrix} \mu_1^i \\ \mu_2^i \\ \vdots \\ \mu_5^i \end{bmatrix} + k_1^i \begin{bmatrix} b_{11}^i \\ b_{21}^i \\ \vdots \\ b_{51}^i \end{bmatrix} + k_2^i \begin{bmatrix} b_{12}^i \\ b_{22}^i \\ \vdots \\ b_{52}^i \end{bmatrix} + \ldots + k_5^i \begin{bmatrix} b_{15}^i \\ b_{25}^i \\ \vdots \\ b_{55}^i \end{bmatrix} \quad (54)$$

$$\begin{bmatrix} k_1^i \\ k_2^i \\ \vdots \\ k_5^i \end{bmatrix} = \begin{bmatrix} b_{11}^i & b_{12}^i & \cdots & b_{15}^i \\ b_{21}^i & b_{22}^i & \cdots & b_{25}^i \\ \vdots & \vdots & \ddots & \vdots \\ b_{51}^i & b_{52}^i & \cdots & b_{55}^i \end{bmatrix}^{-1} \begin{bmatrix} \rho_1^i - \mu_1^i \\ \rho_2^i - \mu_2^i \\ \vdots \\ \rho_5^i - \mu_5^i \end{bmatrix} \quad (55)$$

As will be understood from these equations, the coefficient k which defines the basic equation (50) for determining the reflectance ρ at an arbitrary displacement angle α can be determined by entering the reflectances for the five representative displacement angles α(=10, 16, 26, 38, 90). Consequently, by determining the coefficient k from the known reflectances measured on the object, a reflectance at a displacement angle other than the reflectances of the known displacement angles can be derived from the foregoing equations.

The equations (50), (55) become tensor-containing equations if the wavelength $\lambda_i$ is taken into consideration.

[Estimation of Reflectance]

The function of the present embodiment will be explained according to the outline and the principle explained in the foregoing. At first there will be explained an outline of an estimation process in a step 100 shown in FIG. 6.

At first a wavelength i is determined (procedure 1), then first to fifth principal component vectors {$b_1, b_2, \ldots, b_5$} are determined from the equation (45) utilizing samples j=1, 2, ..., N N (procedure 2), then reflectances $\rho_{10}^i, \rho_{16}^i, \rho_{26}^i, \rho_{38}^i, \rho_{90}^i$ at the displacement angles (10, 16, 26, 38, 90) in an arbitrary object are entered in the equation (55) to determine the coefficient {$k_1, k_2, \ldots, k_5$} (procedure 3), then the equation (50) is used to determine the displacement angles (10, 16, 26, 38, 90) at the wavelength $\lambda_i$ (procedure 4), and these procedures are repeated for all the wavelengths {$\lambda_1, \lambda_2, \ldots$} (procedure 5).

Figure 9:
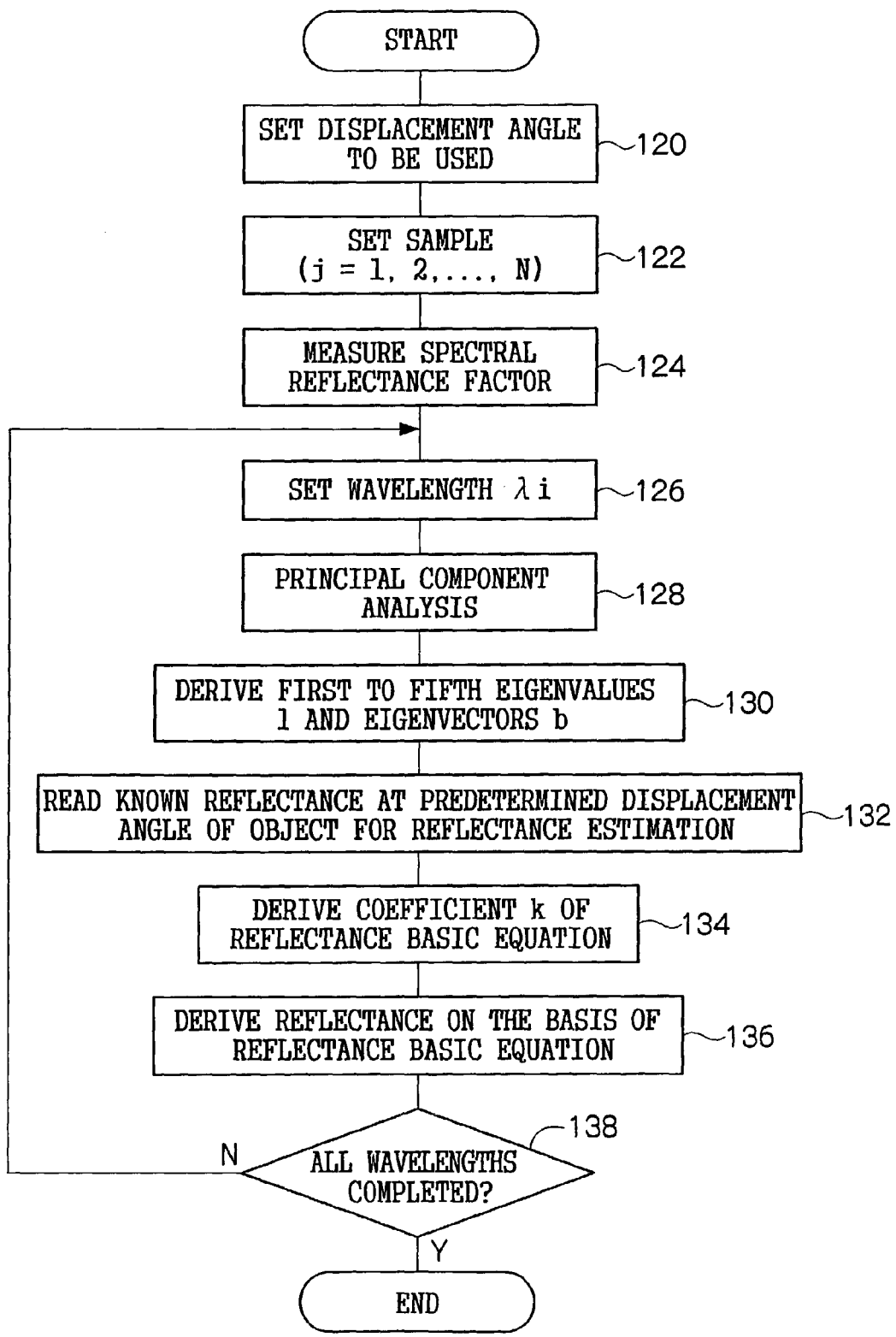
FIG. 9 is a flow chart showing the flow of a reflectance estimating process by a principal component analysis taking luminocity or brightness into consideration, in a second embodiment of the present invention.

In more details, in the reflectance estimation (principal displacement angle estimation) process of the step 100 for a displacement angle of 100 or larger, a process routine shown in FIG. 9 is executed.

Figure 10:
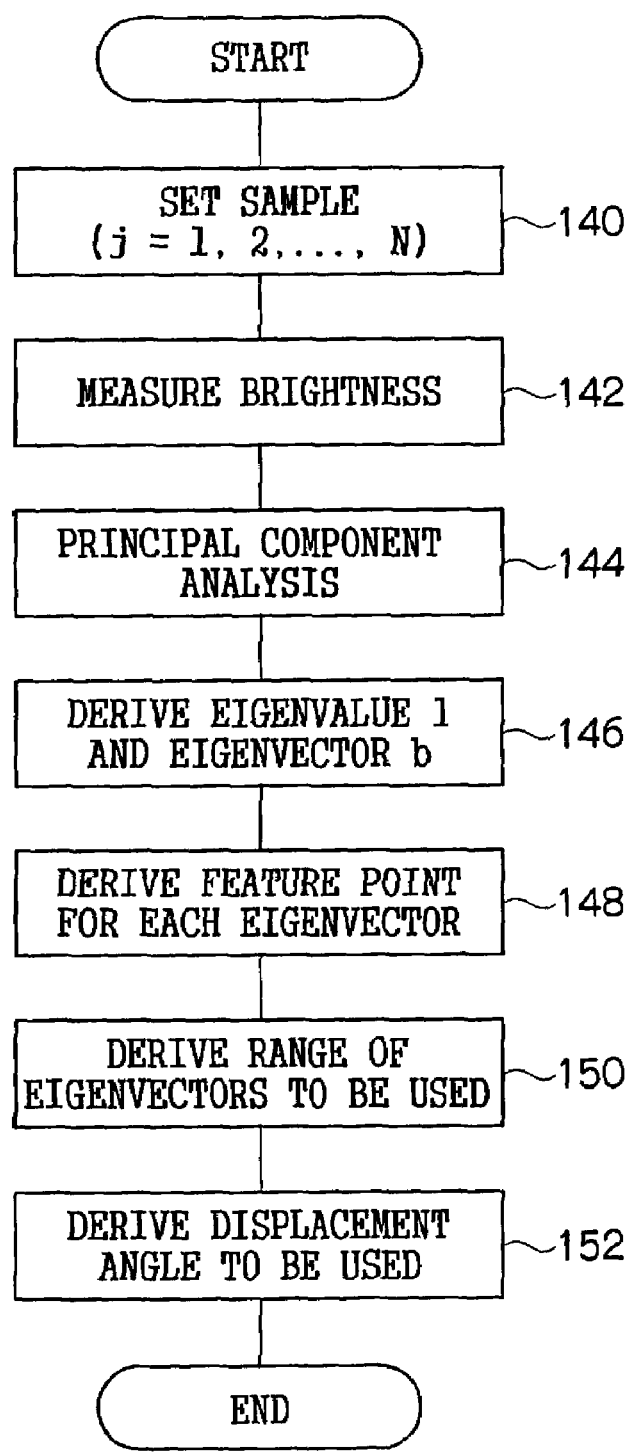
FIG. 10 is a flow chart showing the flow of a displacement angle determining process in a second embodiment of the present invention.
Figure 11:
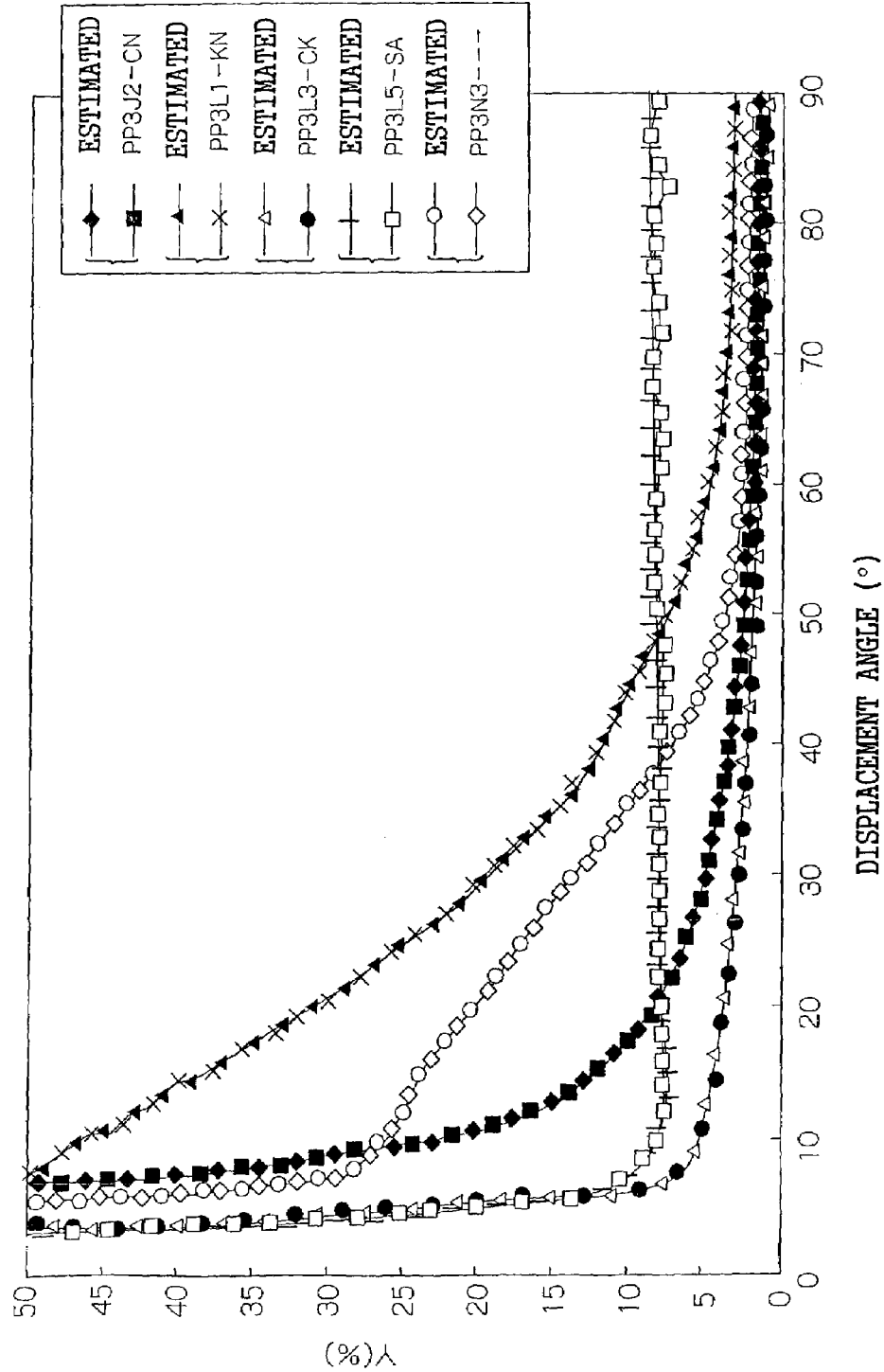
FIG. 11 is a characteristic chart showing characteristics of reflectance including estimation of reflectance by a principal component analysis on different samples, and characteristics of reflectance of measured examples of displacement angles over 0° to 90°.
Figure 12:
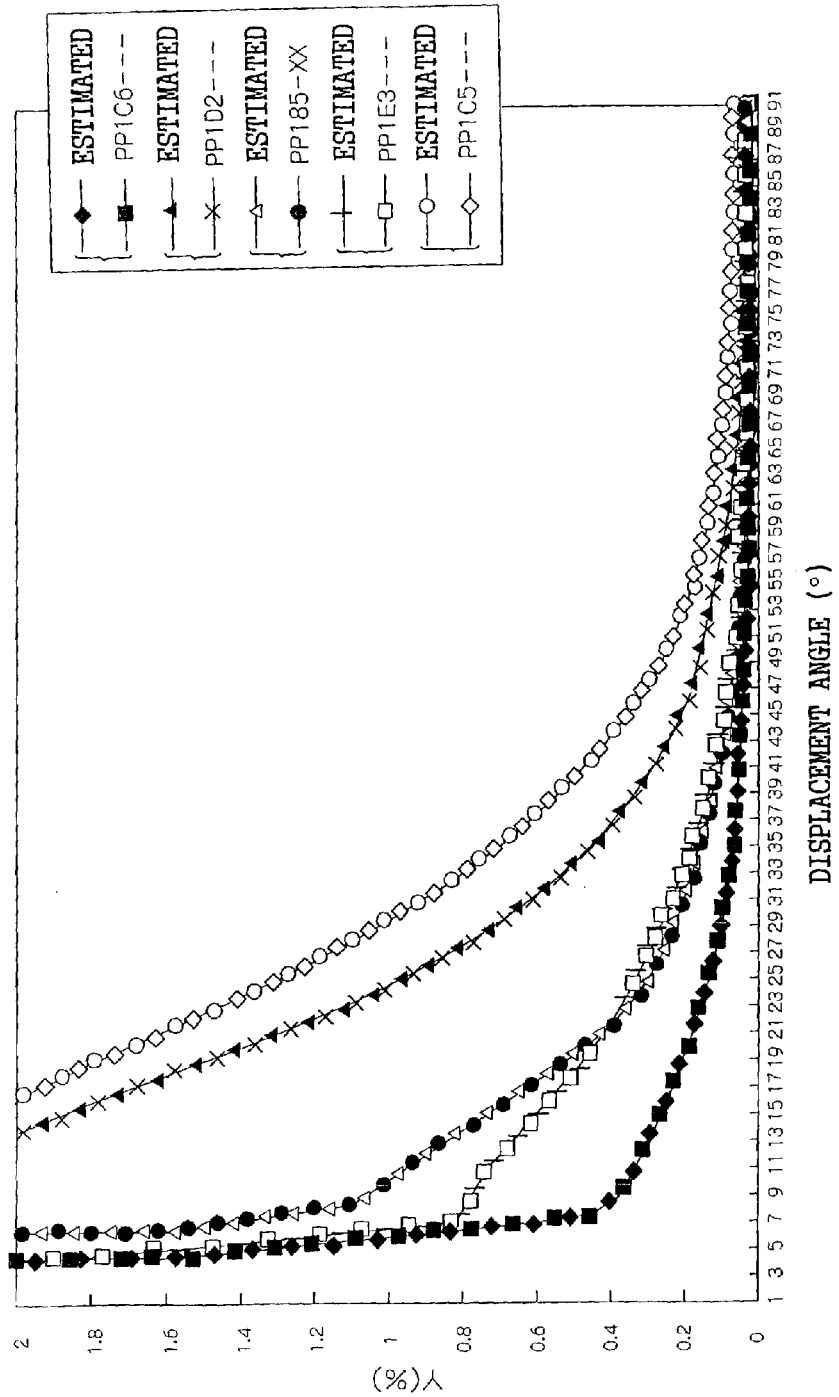
FIG. 12 is a characteristic chart showing characteristics of reflectance including estimation of reflectance by a principal component analysis on samples different from those in FIG. 11, and characteristics of reflectance of measured examples for displacement angles over 0° to 90°.
Figure 13:
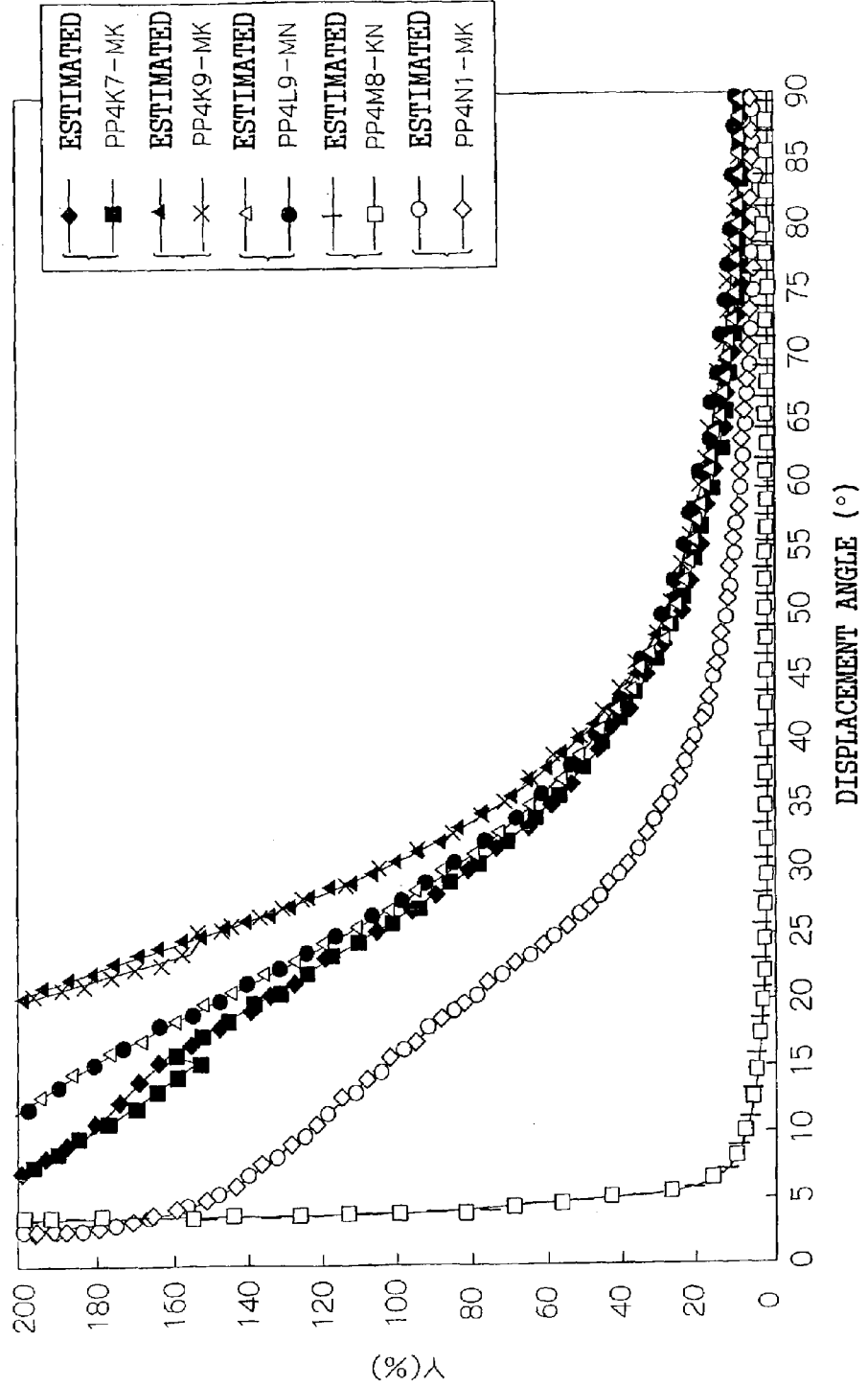
FIG. 13 is a characteristic chart showing characteristics of reflectance including estimation of reflectance by a principal component analysis on samples different from those in FIGS. 11 and 12, and characteristics of reflectance of measured examples for displacement angles over 0° to 90°.
Figure 14:
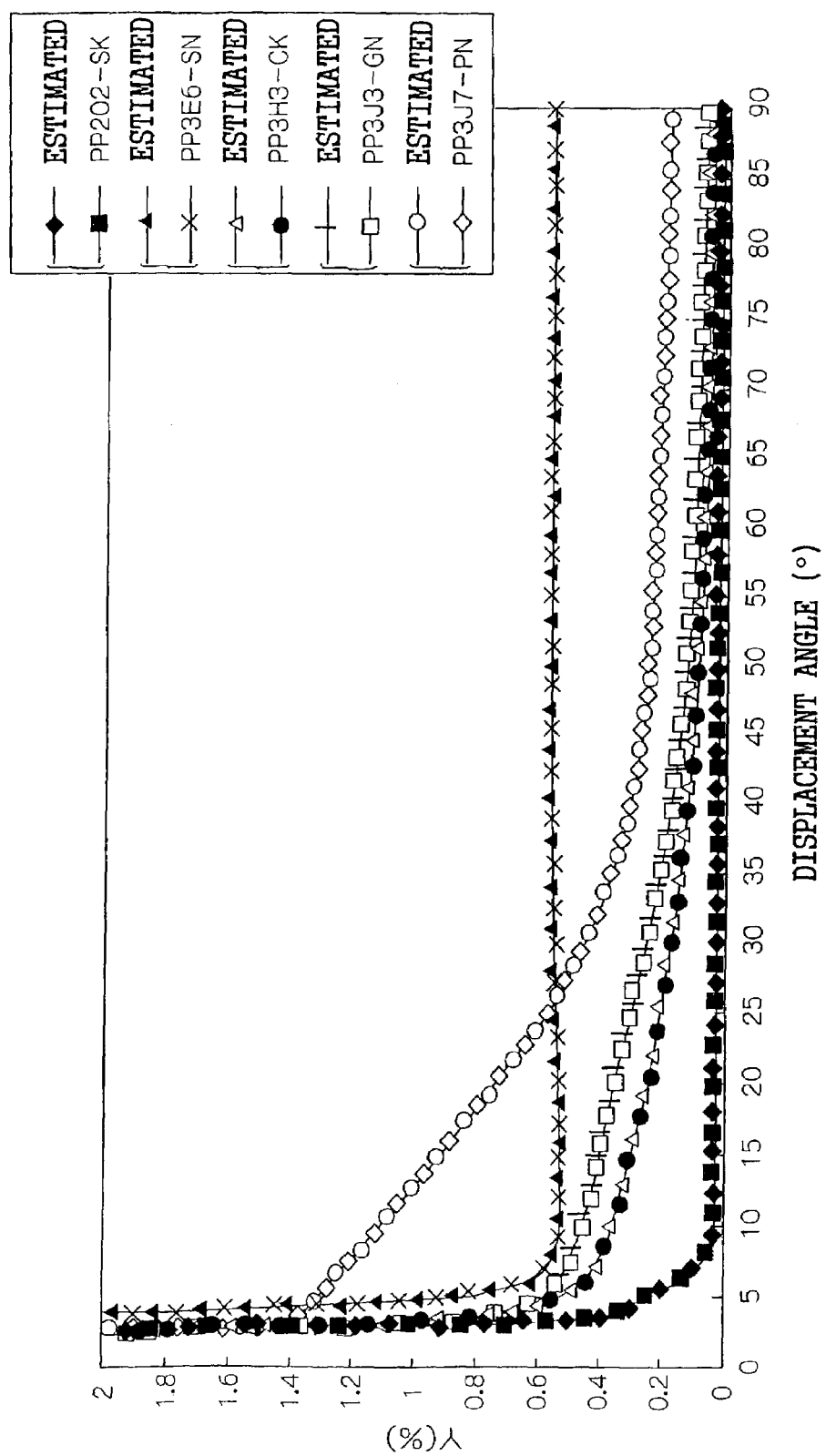
FIG. 14 is a characteristic chart showing characteristics of reflectance including estimation of reflectance by a principal component analysis on samples different from those in FIGS. 11 to 13, and characteristics of reflectance of measured examples for displacement angles over 0° to 90°.

A step 120 executes a process routine shown in FIG. 10, as a displacement angle setting process explained in the foregoing principle. Referring to FIG. 10, a step 140 sets samples (j=1, 2, ..., N) for obtaining lightmeasurement data, and a next step 142 measures the luminocity of each sample. The luminocity may be measured with a measuring device, or may be obtained by reading data of measured values, or entered from a keyboard. A next step 144 initiates a principal component analysis utilizing the luminocity Y shown in the equations (51), (52) as explained in the principle of the reflectance estimation, and a step 146 derives an engenvalue 1 and an eigenvector b obtained by the principal component analysis. The step 146 also derives an average vector μ.

A next step 148 derives, in the result of the principal component analysis, a feature point representing the feature of each principal component vector. The feature point is a maximum or minimum value in the characteristics of each principal component vector, and is determined a predetermined principal component vector (fourth principal component vector in the present embodiment). There is also determined a cumulative contribution factor.

A next step 150 determines a range of the eigenvectors to be utilized. This is a process for determining the principal component vectors providing a cumulative contribution factor of a predetermined value or higher, and, in the present embodiment, derivation is executed down to the fourth principal component vector providing a cumulative contribution factor of 99.98%. A next step 152 derives feature points down to the fourth principal component vector, namely displacement angles to be utilized (in the present embodiment, five displacement angles of 10°, 90°, 26°, 38° and 16°).

After the setting of the displacement angles to be utilized, the sequence proceeds to a step 122 in FIG. 9, for setting samples (j=1, 2, . . . , N) for obtaining the light measurement data, and a next step 124 executes measurement of the reflectance. The reflectance may be measured with a reflectance measuring device (for example a spectral reflectance factor measuring device), or may be obtained by reading data of measured values, or entered from a keyboard.

A next step 126 sets an arbitrary wavelength $\lambda_t$ (procedure 1), and a step 128 initiates a principal component analysis in a similar manner as explained in the foregoing, and a step 130 derives an engenvalue 1, an eigenvector b and an average vector μ obtained by the principal component analysis. As explained in the foregoing, the step 130 extracts the eigenvalues and the eigenvectors of the first to fifth principal component vectors for calculating the coefficient k (procedure 2).

A next step 132 reads the reflectance of an object which is to be subjected to estimation. The reflectance is measured for five displacement angles set in the foregoing. Based on the read and known reflectances, a step 134 derives the coefficient k, utilizing the aforementioned equation (55) for deriving the coefficient (procedure 3). In this manner there is determined the basic equation for the reflectance, shown in (50). A next step 136 derives the reflectance at an arbitrary displacement angle, based on the basic equation with the coefficient k determined in the step 134 and with p=81 and m=5.

Then a next step 138 discriminates whether the above-described process for the wavelength set in the step 106 has been completed for all the wavelengths, for example all the visible wavelength range (such as 400 to 700 nm), and, if not completed (procedure 5), the above-described process is executed in repetition, but, if completed, the present routine is terminated.

In the present embodiment, the reflectance estimation in the step 20° for an displacement angle less than 10° (estimation in the vicinity of normal reflection) is executed as in the foregoing embodiment.

As explained in the foregoing, the present embodiment is capable, by introducing a concept of luminocity instead of the reflectance, of grasping the feature of the entire wavelength range for example of the visible light, and finding a displacement angle constituting a feature point. It is thus rendered possible to determine the reflectance at an arbitrary displacement angle, based only on data limited to the measured data of the displacement angles constituting the feature points in the reflectance.

FIGS. 11, 12, 13 and 14 show characteristics of reflectance, on different samples, for the displacement angle from 0° to 90° including the estimation by the principal component analysis in the present embodiment and those of the measured values of respective samples. As shown in these charts, there was obtained a result of estimation close to the measured data. It is also understood that the result of estimation has an interpolating function for the measured data. More specifically, the measured data may show a fluctuation, namely a slight variation of the characteristic curve for example by the measuring conditions, but the estimation provides a characteristic reflectance curve showing a continuity with an interpolating effect. This will be ascribable to a fact that the principal component analysis, against a variation in the displacement angle, estimates a reflectance in which the feature of such displacement angle is reflected.

A reflectance estimation for a displacement angle less than 10° has a low reliability because of a larger error, but is still needed for an image display such as CG. In case of an image display with a continuous change in the displacement angle, it is effective to given emphasis on the smooth continuity of the image display.

In the foregoing embodiments, there has been explained a process of inserting or interpolating the measured data as an example. In order to estimate smoothly continuous reflectance behavior, maintaining the behavior of the reflectance within a range of 10° to 90° estimated effectively as explained in the foregoing, there is preferred an extrapolating process employing data obtained by the aforementioned principal component analysis. For such extrapolation process, it is effective to extrapolate the reflectance itself, for example the first to fifth principal component vectors. For such extrapolation, there is known a multiple regression analysis or a time-sequential analysis.

Among such extrapolation processes, the extrapolation of the reflectance itself results in a number of steps, since it has to be executed for each objected surface (painted surface) and for each wavelength. On the other hand, the extrapolation for example of the first to fifth principal component vectors has to be executed similarly for each wavelength, but can be easily achieved for each painted surface if the reflectances for the five displacement angles are obtained.

Therefore, for estimating the reflectance for the displacement angle less than 10°, it is preferable to extrapolate the reflectance itself or the first to fifth principal component vectors.

Third Embodiment

The foregoing embodiments executes an estimation of the reflectance principally for a displacement angle of 10° or larger. The present embodiment is to estimate the reflectance at a displacement angle less than 10°, namely in a vicinity of the normal reflecting direction, where the measured data tend to become unstable. The present embodiment has a configuration approximately similar to that of the foregoing embodiments, wherein parts same as in the foregoing embodiments are represented by same symbols and omitted from the detailed description.

The reflectance at a displacement angle less than 10°, larger in the error component, is excluded in the principal component analysis. However, in the CG, the reflectance at a displacement angle less than 10° is also required for ensuring continuity of the image. The reflectance at a displacement angle less than 10° can be estimated for example by the use of actually measured data or by an interpolation process as explained in the foregoing, but data of a sufficient amount are necessary.

Therefore, the present inventor has made various experiments and has obtained a knowledge that a time-sequential estimation is effective for the estimation with limited data. The present embodiment employs the time-sequential estimation for estimating the reflectance of a displacement angle less than 10°. More specifically, the reflectance estimation by the time-sequential estimation is executed by considering a change in the reflectance resulting from an increase or a decrease of the displacement angle as a time-sequential change. An example of the method effective for such time-sequential estimation is ARIMA (auto regressive integrated moving average) model.

[Estimation of Reflectance: Time-Sequential Estimation for a Displacement Angle Less than 10°]

At first, characteristics of the reflectance at displacement angles of 10° or larger is determined at each displacement angle, as explained in the foregoing embodiments.

Figure 15:
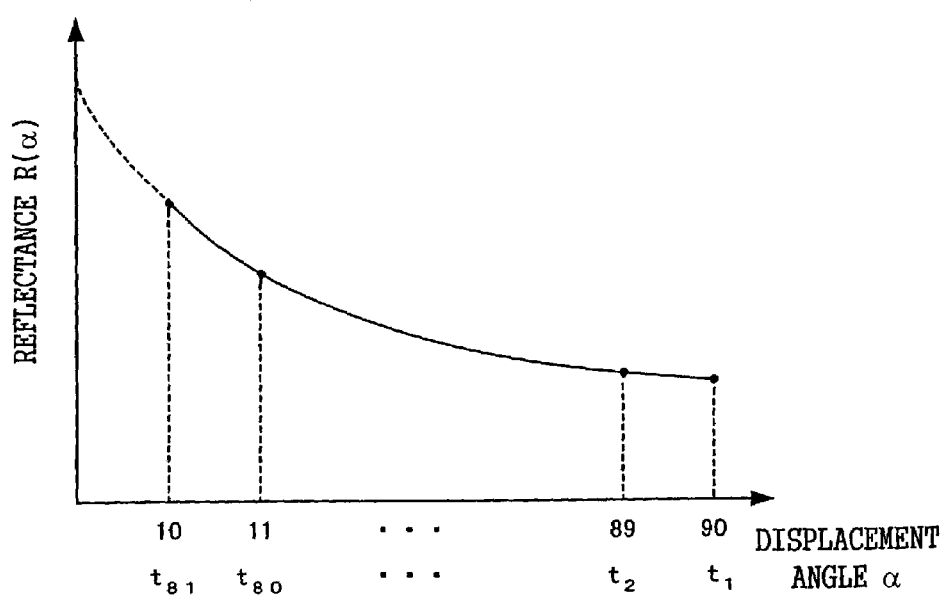
FIG. 15 is a view for explaining a time-sequential estimation of reflectance for a displacement angle less than 10°, according to a third embodiment of the present invention.

Then, as shown in FIG. 15, in the reflectance characteristics in the displacement angles of 10° or higher, a displacement angle at each unit angle (1° in FIG. 15) is made to correspond to a time t. More specifically, there are made correspondences of a time $t_1=90°$, a time $t_2=89°$, ..., a time $t_{80}=11°$ and a time $t_{81}=10°$. Such reflectances $R(\alpha)$ at the times t are used to estimate a reflectance at a displacement angle less than 10°.

At first reflectances R(90) to R(10) at times $t_1$ to $t_{81}$ are used to estimate a reflectance R(9) at a displacement angle 9° corresponding to a time $t_{82}$. Then the reflectances R(90) to R(9) at times $t_1$ to $t_{82}$ are used to estimate a reflectance R(8) at a displacement angle 8° corresponding to a time $t_{83}$. In a similar manner, reflectances R are estimated at displacement angles $\alpha=7, 6, \ldots, 0$.

As the estimation is executed in succession in a decreasing direction of the displacement angle α from 10° for which the estimation is made by the principal component analysis, the reflectance changes smoothly in the vicinity of 10° where the method of estimation is switched. Therefore, in case of an image display such as in CG, there can be assured a continuity of the image.

The time-sequential estimation for example based on actually measured data of the reflectance usually provides a satisfactory result to about 5°, but the reflectance often shows an abrupt increase at a displacement angle in a vicinity of the normal reflecting direction.

Figure 16:
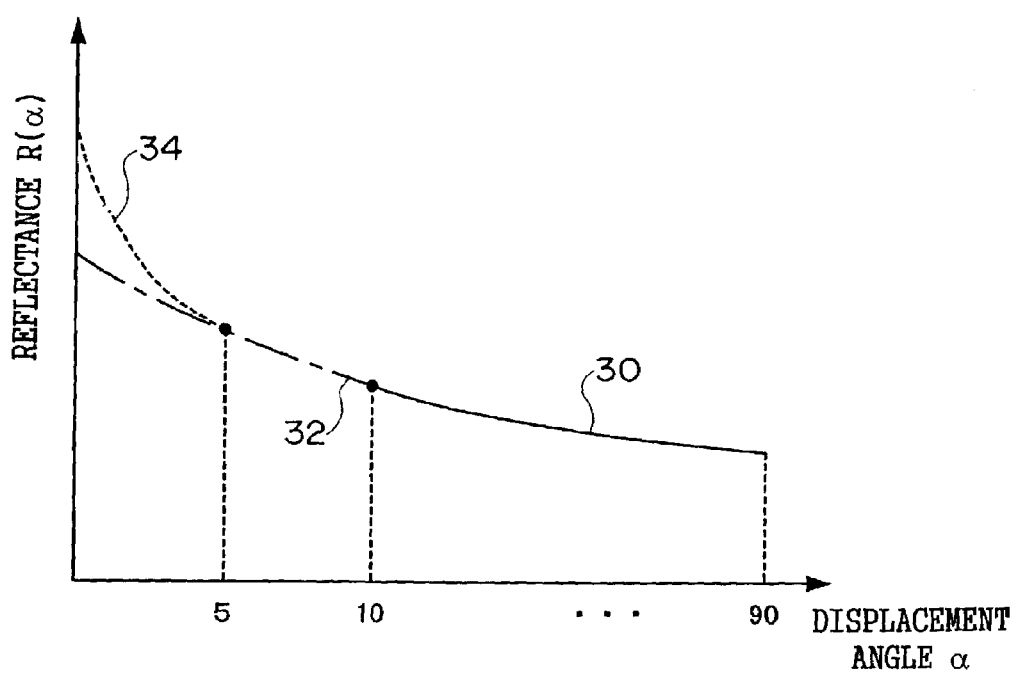
FIG. 16 is a view for explaining an estimation of reflectance by dividing a displacement angle range, according to the third embodiment of the present invention.

It is therefore also possible to divide more finely the displacement angle range in which the reflectance is estimated, as shown in FIG. 16. FIG. 16 shows a case where the reflectance is estimated by a curve approximation (indicated by a curve 34) in a displacement angle range of 0° to 5°, by a time-sequential estimation (indicated by a curve 32) in a displacement angle range of 5° to 10°, and by a principal component analysis (indicated by a curve 30) in a displacement angle range of 10° and larger. Such method allows to achieve a reflectance estimation closer to the measured data. FIG. 16 shows an example of switching the estimating method at a displacement angle α=5°, but such switching is not limited to a displacement angle α=5° but may be made in a vicinity of a displacement angle where the reflectance shows a steep increase.

Fourth Embodiment

The present embodiment provides another method of estimating the reflectance at a displacement angle less than 10°, namely in the vicinity of the normal reflecting direction, by the principal component analysis only. The present embodiment has a configuration approximately similar to that of the foregoing embodiments, wherein parts same as in the foregoing embodiments are represented by same symbols and omitted from the detailed description.

[Estimation of Reflectance: Extrapolation of Principal Component Vectors at a Displacement Angle Less than 10°]

In the foregoing embodiments, the reflectance at a displacement angle less than 10°, larger in the error component, is excluded in the principal component analysis, but, in the present embodiment, the reflectance at a displacement angle less than 10° 0 is also considered to determine the complete principal component vector including a range where the displacement angle α is 0° to 9°, and the reflectance is estimated over a displacement angle range of 0° to 90°, from the foregoing equation (50).

More specifically, the measured data in the displacement angle range of 0° to 9° are used to determine an eigenvalue, an eigenvector (principal component vector), an average vector and a coefficient k, thereby setting the basic equation. Thus the extrapolation of the reflectance for the displacement angle from 0° to 90°, namely the reflectance for the displacement angle α from 0° to 9°, is made possible and the reflectance at each displacement angle can be determined.

Fifth Embodiment

The present embodiment provides another method of estimating the reflectance at a displacement angle less than 10°, namely in the vicinity of the normal reflecting direction, by a multiple regression analysis. The present embodiment has a configuration approximately similar to that of the foregoing embodiments, wherein parts same as in the foregoing embodiments are represented by same symbols and omitted from the detailed description.

[Estimation of Reflectance: Estimation at a Displacement Angle Less than 10° by Multiple Regression Analysis]

The present embodiment estimates the reflectance at a displacement angle α less than 10°, utilizing the measured data of the reflectance in the principal component analysis employed for the displacement angle of 10° or larger as explained in the foregoing and executing a multiple regression analysis.

In the present embodiment, a reflectance $y_i$ at a displacement angle α less than 10° is represented by a following equation:

$$y_i = a_i + b_i y(\alpha) + c_i y(\alpha) + d_i y(\alpha) +$$

wherein a suffix i indicates a displacement angle less than 10°, namely 0, 1, ..., 9. Also displacement angles $\alpha_1, \alpha_2, \alpha_3, \ldots$ indicate arbitrary displacement angles at 10° or larger in the aforementioned principal component analysis. Also $a_i, b_i, c_i, d_i, \ldots$ indicate coefficients for the respective displacement angles.

The present inventor have made estimation of the reflectance by employing all the displacement angles as the arbitrary displacement angles of 10° or larger in the principal component analysis, to be employed in the multiple regression analysis according to the above equation, but has obtained a result that it is preferable, as such displacement angles, to employ the actually measured reflectances at the displacement angles constituting the feature points of the principal component vectors. More specifically, there is obtained a knowledge that there are preferred the displacement angles α of the principal component vectors having a large cumulative contribution factor, and that five displacement angles {10°, 90°, 26°, 38°, 16°} constituting the feature points of the first to fourth principal component vectors should be considered.

Thus, the five displacement angles {10°, 90°, 26°, 38°, 16°} are employed with the reflectance $y_i$ at the displacement angle constituting the feature point as an explanatory variable to determine the reflectance $y_i$ at a displacement angle α less than 10° as a result of analysis. In this manner it is rendered possible to easily estimate the reflectance $y_i$ at a displacement angle α less than 10°.

Also as a result of various experiments, the present inventor has obtained a knowledge that, among the five displacement angles mentioned above, three displacement angles {10°, 26°, 38°} are representative.

Thus, there is obtained a knowledge that the multiple regression analysis is possible by replacing the foregoing equation by a following equation with the displacement angles $α_1=10°$, $α_2=26°$ and $α_3=38°$:

$$y_i = a_i + b_i y(10) + c_i y(26) + d_i y(38)$$

In such multiple regression analysis, the reflectance $y_i$ at the displacement angles $α_1=10°$, $α_2=26°$ and $α_3=38°$ are used as an explanatory variable to determine the reflectance $y_i$ at a displacement angle α less than 10° as a result of analysis.

In this manner it is rendered possible to determine the reflectance in the displacement angle range of 0° to 9° with even fewer measurement data.

In the present embodiment, the reflectance for a displacement angle less than 10° is estimated by the multiple regression analysis, but there may also be executed, instead of the estimation by the multiple regression analysis, an estimation with a neural network or a sequential information interpolating process for intermediate color estimation (for example cf. Japanese Patent No. 3109336 "color reproducing method"). The estimation process by a neutral network is constructed by setting an explanatory variable as an input, also setting a desired variable as an output and executing a study process utilizing the reflectances at the aforementioned displacement angles constituting the feature points and the reflectance for the displacement angle less than 100 as teacher data.

In the foregoing embodiments, there have been explained cases where different estimation methods are employed for the ranges of the displacement angle for which the reflectance is to be estimated, but the present invention is not limited to such cases and the estimation methods in the foregoing embodiments may be used in combination or may be rearranged.

The reflectance estimation in the foregoing embodiments functions effectively also for a solid surface, a metallic surface, a pearl mica surface or another arbitrary painted surface constituting major categories of the painting. It is particularly preferable to classify the surfaces into solid, metallic, pearl mica and others and to execute the reflectance estimating method of the present invention for each classified category. In this manner the precision can be further improved.

Also in the foregoing embodiments, there has been explained a case of estimating the reflectance within a range of the displacement angle from about 0° to about 90°, but the present invention is not limited to such angular range. For example the reflectance estimation may be executed for a displacement angle exceeding about 90° or for a displacement angle less than about 0°. In such case, in order to estimate smoothly continuous reflectance behavior, maintaining the behavior of the reflectance within a range of 10° to 90° estimated effectively as explained in the foregoing, it is preferable to include an extrapolating process employing data obtained by the aforementioned principal component analysis. For such extrapolation process, it is effective to extrapolate the reflectance itself, for example the first to fifth principal component vectors. For such extrapolation, there is known a multiple regression analysis or a time-sequential analysis. Also for a displacement angle less than about 0°, the behavior is considered similar to that for a displacement angle of about 0° or larger, the reflectance of a displacement angle of 0° or larger may be used without change.

As explained in the foregoing, the present invention executes, based on an eigenvector which is a principal component vector indicating the feature of the reflectance obtain by the principal component analysis on the reflectances at predetermined plural displacement angles, a reflectance estimation at a displacement angle other than the predetermined displacement angles, thereby providing an effect that the feature of the reflectance at a displacement angle is reflected also in another displacement angle and the reflectance can be estimated at an arbitrary displacement angle in which such feature of the reflectance is reflected.

What is claimed is:

1. A reflectance estimating method for estimating a reflectance of an object at an angle representing displacement from a normal light reflecting direction of the object, the method comprising:

(a) a step of executing a principal component analysis on reflectances at predetermined plural displacement angles;

(b) a step of selecting a principal component vector obtained by the analysis as an eigenvector;

(c) a step of estimating a reflectance at a displacement angle other than said predetermined displacement angles, at least based on said eigenvector;

(d) a step, with respect to the principal component vector obtained as a result of said principal component analysis, of determining characteristics for each factor of the principal component vector regarding the relationship between a principal component and a displacement angle;

(e) a step of determining a displacement angle corresponding to each of feature points of the determined characteristics; and (f) a step of estimating a reflectance at a displacement angle other than said predetermined displacement angles, based on the determined displacement angle;

and further comprising a step of forming a correspondence between a reflectance distribution of an arbitrary displacement angle and a luminocity including relative luminous efficiency characteristics, and adopting a feature point of characteristics of each term of said principal component vector obtained by said principal component analysis, as a displacement angle to be used.

2. A reflectance estimating method according to claim 1, wherein said plural displacement angles are at least two angles among about 10°, about 16°, about 26°, about 38° and about 90°.

3. A reflectance estimating method according to claim 1, wherein said principal component analysis step (a) includes a step of entering a predetermined reflectance of an object, executing a principal component analysis on such reflectance thereby obtaining a principal component as an eigenvalue and a principal component vector as said eigenvector, and estimating a reflectance at a displacement angle other than said predetermined displacement angles based on said eigenvalue and said eigenvector.

4. A reflectance estimating method according to claim 3, comprising a step of determining a basic equation on said reflectance represented by said eigenvalue, said eigenvector and a coefficient to be multiplied on said eigenvector and estimating, from said basic equation, a reflectance at a displacement angle other than said predetermined displacement angles.

5. A reflectance estimating method according to claim 3, comprising a step of determining a basic equation including an average value vector obtained by a principal component analysis on said reflectances, and estimating, from said basic equation, a reflectance at a displacement angle other than said predetermined displacement angles.

6. A reflectance estimating method for estimating a reflectance of an object at an angle representing displacement from a normal light reflecting direction of the object, the method comprising:
(a) a step of executing a principal component analysis on reflectances of predetermined plural displacement angles within a predetermined angular range;
(b) a step of selecting a principal component vector and a principal component obtained by said principal component analysis respectively as an eigenvector and an eigenvalue, and determining characteristics of the eigenvector on the relationship between the eigenvalue and the displacement angle;
(c) a step of determining a representative displacement angle from the determined characteristics;
(d) a step of predetermining a basic equation on said reflectance, represented by said eigenvalue, said eigenvector and a coefficient to be multiplied on said eigenvector;
(e) a step of determining said coefficient based on said basic equation, said representative displacement angle and a reflectance at said representative displacement angle and defining the basic equation utilizing the determined coefficient and said eigenvector as a calculation equation;
(f) a step of estimating a reflectance at a displacement angle other than said predetermined displacement angles within said predetermined angular range, based on said calculation equation; and
(g) a step of estimating a reflectance of a displacement angle outside said predetermined angular range by extrapolating said eigenvector.

7. A reflectance estimating method according to claim 6, comprising a step, after said estimation of reflectance, of estimating a reflectance for a displacement angle in excess of about 90° by a multiple regression analysis utilizing three displacement angles of about 10° or larger but less than about 90°.

8. A reflectance estimating method according to claim 7, wherein said three displacement angles are about 10°, about 26° and about 38°.

9. A reflectance estimating method for estimating a reflectance ($\rho$) of an object at an angle ($\alpha$) representing displacement from a normal light reflecting direction of the object, the method comprising:
(1) a step of representing a reflectance ($\rho$) at an arbitrary displacement angle by a predetermined basic equation including an average value vector ($\mu$), an eigenvector (b) and a coefficient k;
(2) a step of setting an arbitrary wavelength ($\lambda 1$);
(3) a step of executing a principal component analysis, at said arbitrary wavelength, on reflectances at predetermined plural displacement angles, thereby obtaining the eigenvector b and the average value vector $\mu$ corresponding to each of the reflectances;
(4) a step of deriving a coefficient k utilizing a result obtained in said step (3) and the known reflectance of the object of which reflectance is to be estimated; and
(5) a step of estimating a reflectance at a displacement angle other than said predetermined displacement angles, based on said basic equation employing said derived coefficient k.

10. A reflectance estimating method for estimating a reflectance of an object at an angle representing displacement from a normal light reflecting direction of the object, the method comprising:
(a) forming a correspondence between a reflectance and a luminosity including a relative luminous efficiency and executing a principal component analysis using a premeasured luminosity;
(b) selecting a principal component vector obtained as a result of the analysis as an eigenvector, obtaining predetermined plural displacement angles at least based on said eigenvector, and measuring only reflectance for a displacement angle at a desired wavelength;
(c) determining, based on only the reflectance obtained by said measuring step, a coefficient to represent the reflectance including a component corresponding to the eigenvector multiplied by said coefficient and estimating, based on the determined coefficient and the eigenvector, a reflectance for a displacement angle other than said predetermined displacement angles at a desired wavelength;
(d) determining, with respect to the principal component vector obtained as a result of said principal component analysis, characteristics representing the relationship between a principal component and a displacement angle for each factor of the principal component vector, determining a displacement angle corresponding to each of feature points of the determined characteristics by selecting as a feature point a correspondence in which the principal component becomes at least one of maximum and minimum values at each of the feature points of the determined characteristics, and
(e) estimating a reflectance at a displacement angle other than said predetermined displacement angles based on the determined displacement angle.

11. A reflectance estimating method according to claim 10, further comprising forming a correspondence between a reflectance distribution of an arbitrary displacement angle and a luminosity including relative luminous efficiency characteristics, and determining a displacement angle corresponding to said feature point of the characteristics representing the relationship between a principal component and a displacement angle or each factor of said principal component vector obtained by executing the principal component analysis.

12. A reflectance estimating method according to claim 10, wherein said displacement angle is a plurality of displacement angles.

13. A reflectance estimating method according to claim 10, wherein said reflectance is estimated for a displacement angle of about 10° or larger.

14. A reflectance estimating method according to claim 12, wherein said plurality of displacement angles comprise at least two angles from the group consisting of about 10°, about 16°, about 26°, about 38°, and about 90°.

15. A reflectance estimating method according to claim 13, wherein after estimation of said reflectance, a reflectance for a displacement angle less than about 10° is estimated by a multiple regression analysis utilizing three displacement angles of about 10° or larger.

16. A reflectance estimating method according to claim 13, wherein after estimation of said reflectance, a reflectance for a displacement angle in excess of about 90° is estimated by a multiple regression analysis utilizing three displacement angles of about 10° or larger but less than about 90°.

17. A reflectance estimating method according to claim 15, wherein said three displacement angles are about 10°, about 26° and about 30°.

* * * * *

UNITED STATES PATENT AND TRADEMARK OFFICE
CERTIFICATE OF CORRECTION

PATENT NO. : 7,283,244 B2  Page 1 of 1
APPLICATION NO. : 10/411276
DATED : October 16, 2007
INVENTOR(S) : Atsushi Takagi It is certified that error appears in the above-identified patent and that said Letters Patent is hereby corrected as shown below:

Claim 9, column 28, line 9, "($\lambda$1);" should read --($\lambda_i$);--

Signed and Sealed this

Fourth Day of March, 2008

JON W. DUDAS
*Director of the United States Patent and Trademark Office*